United States Patent
Kaneko et al.

(10) Patent No.: US 10,012,631 B2
(45) Date of Patent: Jul. 3, 2018

(54) FLUORESCENCE SENSOR FOR TARGET ANALYSIS, KIT FOR TARGET ANALYSIS, AND TARGET ANALYSIS METHOD USING SAME

(71) Applicant: NEC Solution Innovators, Ltd., Tokyo (JP)

(72) Inventors: Naoto Kaneko, Tokyo (JP); Ikuo Shiratori, Tokyo (JP); Katsunori Horii, Tokyo (JP); Jou Akitomi, Tokyo (JP); Iwao Waga, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 0 days.

(21) Appl. No.: 14/906,897

(22) PCT Filed: Jun. 27, 2014

(86) PCT No.: PCT/JP2014/067125
§ 371 (c)(1),
(2) Date: Jan. 21, 2016

(87) PCT Pub. No.: WO2015/012059
PCT Pub. Date: Jan. 29, 2015

(65) Prior Publication Data
US 2016/0146772 A1 May 26, 2016

(30) Foreign Application Priority Data
Jul. 23, 2013 (JP) .................................. 2013-152476

(51) Int. Cl.
*C12Q 1/68* (2018.01)
*G01N 33/04* (2006.01)
(Continued)

(52) U.S. Cl.
CPC ............. *G01N 33/04* (2013.01); *C12N 15/11* (2013.01); *C12N 15/115* (2013.01);
(Continued)

(58) Field of Classification Search
CPC ......... C12M 1/34; C12Q 1/68; G01N 33/542; C12N 15/115
See application file for complete search history.

(56) References Cited

U.S. PATENT DOCUMENTS

| 5,424,186 A | 6/1995 | Fodor et al. |
| 5,807,522 A | 9/1998 | Brown et al. |

(Continued)

FOREIGN PATENT DOCUMENTS

| CN | 101809164 A | 8/2010 |
| EP | 2 463 660 A1 | 6/2012 |

(Continued)

OTHER PUBLICATIONS

International Search Report, Corresponding to PCT JP2014/067125, dated Jul. 29, 2014, 1 page.
(Continued)

*Primary Examiner* — Narayan Bhat
(74) *Attorney, Agent, or Firm* — Wilmer Cutler Pickering Hale and Dorr LLP

(57) ABSTRACT

The present invention is intended to provide a novel fluorescence sensor for target analysis, a kit for target analysis, and a target analysis method using the same.
The fluorescence sensor for target analysis according to the present invention includes a nucleic acid molecule that includes a G-quartet-forming nucleic acid region (D) that forms a G-quartet and a binding nucleic acid region (A) that binds to a target. In the absence of a target, formation of a G-quartet in the G-quartet-forming nucleic acid region (D) is inhibited. In the presence of a target, the target comes into
(Continued)

contact with the binding nucleic acid region (A), the G-quartet is formed in the G-quartet-forming nucleic acid region (D) due to the contact, the G-quartet-forming region (D) and porphyrin forms a complex, and the complex generates fluorescence.

17 Claims, 8 Drawing Sheets

(51) Int. Cl.

| | | |
|---|---|---|
| *C12N 15/115* | (2010.01) | |
| *G01N 33/542* | (2006.01) | |
| *C12Q 1/6825* | (2018.01) | |
| *C12N 15/11* | (2006.01) | |

(52) U.S. Cl.
CPC ......... *C12Q 1/6825* (2013.01); *G01N 33/542* (2013.01); *C12N 2310/127* (2013.01); *C12N 2310/151* (2013.01); *C12N 2310/16* (2013.01); *C12N 2310/3519* (2013.01)

(56) References Cited

U.S. PATENT DOCUMENTS

| | | | |
|---|---|---|---|
| 6,110,426 A | 8/2000 | Shalon et al. | |
| 7,378,236 B1 | 5/2008 | Brown et al. | |
| 9,880,174 B2 * | 1/2018 | Horii | G01N 33/6845 |
| 2012/0202195 A1 | 8/2012 | Waga et al. | |
| 2015/0056720 A1 * | 2/2015 | Horii | C12Q 1/008 |
| | | | 436/501 |

FOREIGN PATENT DOCUMENTS

| | | | |
|---|---|---|---|
| JP | H-10-503841 A | | 4/1998 |
| WO | WO-2008/122088 A1 | | 10/2008 |
| WO | WO-2011/016565 A1 | | 2/2011 |
| WO | WO 2013/140629 | * | 9/2013 |
| WO | WO 2013/0140681 | * | 9/2013 |
| WO | WO 2014/041024 | * | 3/2014 |

OTHER PUBLICATIONS

Cheng et al., Biochemistry, vol. 48, pp. 7817-7823, 2009, 7 pp.
Kaneko et al., Molecular Biology Society of Japan "MBSJ", Annual Meeting, 2012, vol. 35, p. 3P-0757, (English Translation), 2 pp.
Liang et al., J. Fluoresce, vol. 21, pp. 1907-1912, 2011, 6 pp.
Li et al., Analytical Chemistry, vol. 81, No. 6, pp. 2144-2149, 2009, 7 pp.
Ren et al., Analytical and Bioanalytical Chemistry, vol. 399, pp. 2763-2770, 2011, 8 pp.
Oh et al., PNAS, vol. 107, No. 32, pp. 14053-14058, 2010, 6 pp.
Teller et al., Analytical Chemistry, vol. 81, No. 21, pp. 9114-9119, 2009, 6 pages.
Travascio et al., Chemistry & Biology, vol. 5, No. 9, pp. 505-517, 1998, 13 pp.
Zhang et al., Analytical Chemistry, vol. 84, No. 11, pp. 4789-4797, 2012, 9 pp.
Chinese Office Action issued by the State Intellectual Property Office of People's Republic of China for Chinese Application No. 201480041690.3 dated May 12, 2017 (14 pages).

* cited by examiner

SEQUENCE LISTING

```
<160> NUMBER OF SEQ ID NOS: 50

<210> SEQ ID NO 1
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 1
tcagggacgg gngtggaggg tga                                              23

<210> SEQ ID NO 2
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 2
acagggacgg gngtggaggg tgt                                              23

<210> SEQ ID NO 3
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 3
caagggacgg gngtggaggg ttg                                              23

<210> SEQ ID NO 4
<211> LENGTH: 23
<212> TYPE: DNA
<213> ORGANISM: Artificial Sequence
<220> FEATURE:
<223> OTHER INFORMATION: nucleic acid sequence
<220> FEATURE:
```

```
<221> NAME/KEY: misc_feature
<222> LOCATION: (12)..(12)
<223> OTHER INFORMATION: n is a, c, g, or t

<400> SEQUENCE: 4
ccagggacgg gngtggaggg tgg                                              23

<210> SEQ ID NO 5
<211> LENGTH: 21
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 5
cagggacggg ngtggagggt g                                                21

<210> SEQ ID NO 6
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 6
cacgggacgg gngtggaggg gtg                                              23

<210> SEQ ID NO 7
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 7
gcagggacgg gngtggaggg tgc                                              23

<210> SEQ ID NO 8
<211> LENGTH: 21
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 8
aagggacggg ngtggagggt t                                                21

<210> SEQ ID NO 9
<211> LENGTH: 23
<212> TYPE: DNA
<213> ORGANISM: Artificial Sequence
<220> FEATURE:
<223> OTHER INFORMATION: nucleic acid sequence
```

```
<220> FEATURE:
<221> NAME/KEY: misc_feature
<222> LOCATION: (12)..(12)
<223> OTHER INFORMATION: n is a, c, g, or t

<400> SEQUENCE: 9
ctagggacgg gngtggaggg tag                                              23

<210> SEQ ID NO 10
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 10
taagggacgg gngtggaggg tta                                              23

<210> SEQ ID NO 11
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 11
aacgggacgg gngtggaggg gtt                                              23

<210> SEQ ID NO 12
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 12
ttagggacgg gngtggaggg taa                                              23

<210> SEQ ID NO 13
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 13
ccggggacgg gngtggaggg cgg                                              23

<210> SEQ ID NO 14
<211> LENGTH: 21
<212> TYPE: DNA
<213> ORGANISM: Artificial Sequence
<220> FEATURE:
```

```
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 14
tagggacggg ngtggagggt a                                                  21

<210> SEQ ID NO 15
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 15
aaagggacgg gngtggaggg ttt                                                23

<210> SEQ ID NO 16
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 16 tagggacgg gngtggaggg cta                                                 23

<210> SEQ ID NO 17
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 17
atagggacgg gngtggaggg tat                                                23

<210> SEQ ID NO 18
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 18
ggggacgggn gtggagggc                                                     19

<210> SEQ ID NO 19
<211> LENGTH: 21
<212> TYPE: DNA
<213> ORGANISM: Artificial Sequence
```

```
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 19
gggggacggg ngtggagggc c                                              21

<210> SEQ ID NO 20
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 20
gaagggacgg gngtggaggg ttc                                            23

<210> SEQ ID NO 21
<211> LENGTH: 23
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (12)..(12)
<223> OTHER INFORMATION: n is a, c, g, or t

<400> SEQUENCE: 21
caggggacgg gngtggaggg ctg                                            23

<210> SEQ ID NO 22
<211> LENGTH: 21
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 22
gtgggacggg ngtggaggga c                                              21

<210> SEQ ID NO 23
<211> LENGTH: 17
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (9)..(9)
<223> OTHER INFORMATION: n is a, c, g, or t

<400> SEQUENCE: 23
gggacgggng tggaggg                                                   17

<210> SEQ ID NO 24
<211> LENGTH: 19
<212> TYPE: DNA
```

```
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 24
agggacgggn gtggagggt                                                    19

<210> SEQ ID NO 25
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 25
agggtggagn gggtagggt                                                    19

<210> SEQ ID NO 26
<211> LENGTH: 18
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 26
agggtgaggn gggagggt                                                     18

<210> SEQ ID NO 27
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 27
agggtgaggn gggccgggt                                                    19

<210> SEQ ID NO 28
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 28
agggtgaggn gggtagggt                                                    19

<210> SEQ ID NO 29
<211> LENGTH: 19
```

-continued

```
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 29
agggtgaggn ggggttgggt                                              19

<210> SEQ ID NO 30
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 30
agggttgagg ngggtgggt                                               19

<210> SEQ ID NO 31
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 31
agggtgaggn gggaggggt                                               19

<210> SEQ ID NO 32
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 32
agggttggag ngggagggt                                               19

<210> SEQ ID NO 33
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 33
aggggtgagg ngggagggt                                               19

<210> SEQ ID NO 34
```

```
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 34
agggttgagg ngggagggt                                                    19

<210> SEQ ID NO 35
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 35
agggtgaggn gggacgggt                                                    19

<210> SEQ ID NO 36
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 36
agggtggagn gggttgggt                                                    19

<210> SEQ ID NO 37
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 37
agggttggag ngggtgggt                                                    19

<210> SEQ ID NO 38
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 38
agggtgaggn gggatgggt                                                    19
```

```
<210> SEQ ID NO 39
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 39
agggtgaggn gggcagggt                                                    19

<210> SEQ ID NO 40
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 40
agggtgcggn gggtagggt                                                    19

<210> SEQ ID NO 41
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 41
agggtggagn gggccgggt                                                    19

<210> SEQ ID NO 42
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 42
agggtgaggn gggctgggt                                                    19

<210> SEQ ID NO 43
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 43
agggtgaggn gggaagggt                                                    19
```

<210> SEQ ID NO 44
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 44
agggttgagg ngggcgggt                                                19

<210> SEQ ID NO 45
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 45
agggttggag nggggpggt                                                19

<210> SEQ ID NO 46
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (10)..(10)
<223> OTHER INFORMATION: n is a, c, g, or t

<400> SEQUENCE: 46
agggtgtggn gggttgggt                                                19

<210> SEQ ID NO 47
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 47
aggggtgagg ngggtgggt                                                19

<210> SEQ ID NO 48
<211> LENGTH: 19
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 48
agggtcgagg ngggtgggt                                                19

```
<210> SEQ ID NO 49
<211> LENGTH: 20
<212> TYPE: DNA
<213> ORGANISM: Artificial Sequence
<220> FEATURE:
<223> OTHER INFORMATION: nucleic acid sequence
<220> FEATURE:
<221> NAME/KEY: misc_feature
<222> LOCATION: (11)..(11)
<223> OTHER INFORMATION: n is a, c, g, or t

<400> SEQUENCE: 49
cagggtgagg ngggagggtg                                              20

<210> SEQ ID NO 50
<211> LENGTH: 60
<212> TYPE: DNA
<213> ORGANISM: Artificial Sequence
<220> FEATURE:
<223> OTHER INFORMATION: nucleic acid sequence

<400> SEQUENCE: 50
tgggtgggag ggtcgggccc tcccgctttt ttttttttttt ttttttttttt tttttttgcgg     60
```

FLUORESCENCE SENSOR FOR TARGET ANALYSIS, KIT FOR TARGET ANALYSIS, AND TARGET ANALYSIS METHOD USING SAME

CROSS-REFERENCE TO RELATED APPLICATIONS

The present application is a national stage application of International Application No. PCT/JP2014/067125 entitled "Fluorescence Sensor for Target Analysis, Kit for Target Analysis, and Target Analysis Method Using Same" filed on Jun. 27, 2014, which claims the benefit of priority from Japanese Patent Application No. JP2013-152476, filed on Jul. 23, 2013, the disclosures of which are incorporated herein in their entirety by reference thereto.

TECHNICAL FIELD

The present invention relates to a fluorescence sensor for target analysis, a kit for target analysis, and a target analysis method using the same.

BACKGROUND ART

There is a demand for detection of a target in various fields such as a clinical treatment field, a food field, and an environment field. For the detection of a target, commonly, a method using an antibody that specifically binds to the target is widely used as a method that utilizing an interaction with the target. In these years, a method using a nucleic acid molecule (so called aptamer) that is specific to the target instead of the antibody is newly developed.

As the method using the aptamer, for example, a sensor in which an aptamer and DNAzyme are linked is reported. DNAzyme is a DNA molecule which activates the catalytic activity of a redox reaction similar to peroxidase or the like when it forms a G-quartet. According to such a sensor, it is possible to indirectly detect a target by binding a target to the aptamer and measuring the catalytic activity of the DNAzyme in a sensor in which the target is bound to the aptamer (Non-Patent Document 1).

It is also reported that G-quartet-formed DNAzyme generates fluorescence when it forms a complex with porphyrin (Non-Patent Documents 2 and 3). Hence, newly reported is a method of detecting a target by not measuring the catalytic activity of a redox reaction of DNAzyme but measuring fluorescence generated by the formation of complex in a sensor in which an aptamer and DNAzyme are linked. However, provision of a fluorescence sensor having a novel structure more suitable in practical use is desired.

CITATION LIST

Non-Patent Document(s)

Non-Patent Document 1: Teller et al., Anal. Chem., 2009, vol. 81, pp. 9114-9119
Non-Patent Document 2: Jiangtao Ren et al., Anal. Bioanal. Chem., 2011, 399, pp. 2763-2770
Non-Patent Document 3: Seung Soo Oh et al., PNAS, 2010, vol. 107, 32, pp. 14053-14058

SUMMARY OF INVENTION

Problem to be Solved by the Invention

Hence, the present invention is intended to provide a novel fluorescence sensor for target analysis, a kit for target analysis, and a target analysis method using the same.

Means for Solving Problem

The present invention provides a fluorescence sensor for target analysis, including at least one nucleic acid molecule selected from the group consisting of the following (I), (II), (III), (IV), and (V) each including a G-quartet-forming region (D) that forms a G-quartet and a binding region (A) that binds to a target, wherein in the absence of a target, formation of a G-quartet in the G-quartet-forming region (D) is inhibited, and in the presence of a target, the target comes into contact with the binding region (A), the G-quartet is formed in the G-quartet-forming region (D) due to the contact, the G-quartet-forming region (D) and porphyrin form a complex, and the complex generates fluorescence:

(I) a single-stranded nucleic acid molecule including the G-quartet-forming region (D), a blocking region (B), and the binding region (A) in this order, wherein the blocking region (B) is complementary to a partial region (Dp) of the G-quartet-forming region (D), and a terminal region (Ab) of the binding region (A) on a blocking region (B) side is complementary to an adjacent region (Df) of the partial region (Dp) of the G-quartet-forming region (D) and is also complementary to a terminal region (Af) of the binding region (A) on an opposite side of the blocking region (B) side;

(II) a single-stranded nucleic acid molecule including the G-quartet-forming region (D), a blocking region (B), the binding region (A), and a stabilizing region (S) in this order, wherein the blocking region (B) is complementary to a partial region (Dp) of the G-quartet-forming region (D), and a terminal region (Ba) of the blocking region (B) on a binding region (A) side is complementary to the stabilizing region (S);

(III) a single-stranded nucleic acid molecule including the G-quartet-forming region (D), a stem-forming region ($S_D$), the binding region (A), and a stem-forming region ($S_A$), wherein the stem-forming region ($S_D$) includes a sequence complementary to the G-quartet-forming region (D), and the stem-forming region ($S_A$) includes a sequence complementary to the binding region (A);

(IV) a single-stranded nucleic acid molecule including the G-quartet-forming region (D) and the binding region (A), wherein the G-quartet-forming region (D) includes a first region (D1) and a second region (D2) that form a G-quartet, and the first region (D1) is located on one end side of the binding region (A) and the second region (D2) is located on the other end side of the binding region (A); and (V) a double-stranded nucleic acid molecule including a first strand (ss1) and a second strand (ss2), wherein the first strand (ss1) includes the G-quartet-forming region (D) and the binding region (A), and the second strand (ss2) includes a stem-forming region ($S_D$) and a stem-forming region ($S_A$), the stem-forming region ($S_D$) includes a sequence complementary to the G-quartet-forming region (D), and the stem-forming region ($S_A$) includes a sequence complementary to the binding region (A).

The present invention also provides a kit for target analysis, including: a sensor; and a reagent, wherein the sensor is the fluorescence sensor for target analysis according to the present invention, and the reagent includes porphyrin.

The present invention also provides a method for target analysis, including steps of: bringing a sample into contact with the fluorescence sensor for target analysis according to the present invention; and detecting fluorescence generated by a complex of the G-quartet-forming region (D) and porphyrin in the sensor in the presence of porphyrin to detect a target in the sample.

Effects of the Invention

According to the fluorescence sensor for target analysis according to the present invention, a target can be indirectly analyzed in simple and efficient manner by utilizing generation of fluorescence. Therefore, for example, the present invention is very useful for researches and tests in various fields such as a clinical treatment field, a food field, and an environment field.

BRIEF DESCRIPTION OF DRAWINGS

FIG. 8A shows the results of reaction solutions each containing a melamine sensor; and FIG. 8B shows the results of reaction solutions each containing no melamine sensor.

FIG. 9A shows the results of reaction solutions each containing a melamine sensor; and FIG. 9B shows the results of reaction solutions each containing no melamine sensor.

DESCRIPTION OF EXEMPLARY EMBODIMENT

Figure 1:
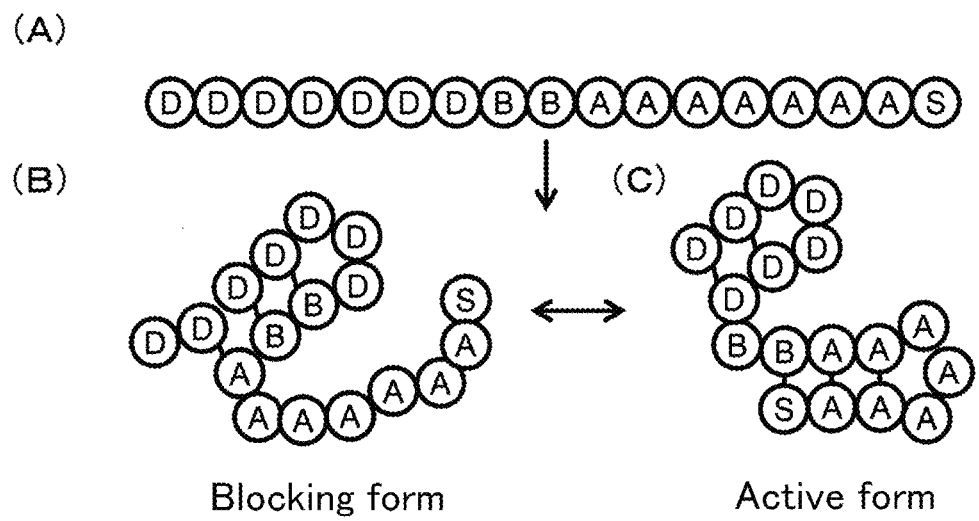
FIGS. 1A to 1C are schematic views showing an example of a nucleic acid molecule in the sensor of the present invention.

In the fluorescence sensor according to the present invention, for example, the single-stranded nucleic acid molecule (I) or (II) includes the G-quartet-forming region (D), the blocking region (B), and the binding region (A) from the 5' side in this order.

In the fluorescence sensor according to the present invention, for example, the single-stranded nucleic acid molecule (III) includes the stem-forming region ($S_D$) and the stem-forming region ($S_A$) as the stem-forming region (S), the G-quartet-forming region (D) and the stem-forming region ($S_D$) include sequences complementary to each other, and the binding region (A) and the stem-forming region ($S_A$) include sequences complementary to each other.

In the single-stranded nucleic acid molecule (III) of the fluorescence sensor according to the present invention, for example, the G-quartet-forming region (D), the stem-forming region ($S_D$), the binding region (A), and the stem-forming region ($S_A$) are linked in the following order (1), (2), (3), or (4):

(1) in order of the binding region (A), the stem-forming region ($S_D$), the G-quartet-forming region (D), and the stem-forming region ($S_A$);

(2) in order of the stem-forming region ($S_A$), the G-quartet-forming region (D), the stem-forming region ($S_D$), and the binding region (A);

(3) in order of the G-quartet-forming region (D), the stem-forming region ($S_A$), the binding region (A), and the stem-forming region ($S_D$); or (4) in order of the stem-forming region ($S_D$), the binding region (A), the stem-forming region ($S_A$), and the G-quartet-forming region (D).

In the single-stranded nucleic acid molecule (IV) of the fluorescence sensor according to the present invention, for example, the first region (D1) and the second region (D2) include sequences complementary to each other at ends on an opposite side of a position of the binding region (A).

The fluorescence sensor according to the present invention includes, for example, a linker sequence between the G-quartet-forming region (D) and the binding region (A).

The fluorescence sensor according to the present invention further includes, for example, a base material. The nucleic acid molecule is disposed on the base material.

In the fluorescence sensor according to the present invention, for example, the nucleic acid molecule is linked to the base material via a linker region.

In the fluorescence sensor according to the present invention, for example, a reagent part that contains a reagent is further disposed on the base material, and the reagent includes porphyrin.

In the fluorescence sensor according to the present invention, for example, the porphyrin is at least one selected from the group consisting of N-Methylmesoporphyrin, Zn-DIGP, ZnPP9, and TMPyP.

In the analysis kit according to the present invention, for example, the sensor is a sensor in which the nucleic acid molecule is disposed on a base material, and a reagent part that contains the reagent is further disposed on the base material.

In the analysis kit according to the present invention, for example, the porphyrin is at least one selected from the group consisting of N-Methylmesoporphyrin, Zn-DIGP, ZnPP9, and TMPyP.

In the analysis method according to the present invention, for example, detection of fluorescence in the detection step is measurement of a fluorescence intensity.

In the analysis method according to the present invention, for example, the sample is at least one selected from the group consisting of raw milk, processed milk, and milk powder.

In the analysis method according to the present invention, for example, the target is melamine.

1. Fluorescence Sensor for Target Analysis

As described above, the sensor for target analysis according to the present invention is characterized in that it includes: at least one nucleic acid molecule selected from the group consisting of the (I), (II), (III), (IV), and (V) each including a G-quartet-forming region (D) that forms a G-quartet and a binding region (A) that binds to a target, wherein in the absence of a target, formation of a G-quartet in the G-quartet-forming region (D) is inhibited, and in the presence of a target, the target comes into contact with the binding region (A), the G-quartet is formed in the G-quartet-forming region (D) due to the contact, the G-quartet-forming region (D) and porphyrin form a complex, and the complex generates fluorescence.

Hereinafter, the sensor for target analysis of the present invention is also referred to as a sensor and the region is also referred to as a nucleic acid region. The single-stranded nucleic acid molecule in the present invention can be referred to as a single-stranded nucleic acid element, for example. Furthermore, in the G-quartet-forming region (D), inhibition of formation of a G-quartet is also referred to as switching-OFF (or turning-OFF) and formation of a G-quartet is also referred to as switching-ON (or turning-ON).

The G-quartet (also referred to as G-tetrad) is commonly known as a planar structure formed of four G (guanine) bases. In the present invention, the G-quartet-forming region (D) includes a plurality of G bases and forms a G-quartet of the plurality of G bases therein. In the present invention, the G-quartet can be either a parallel type or an antiparallel type, for example. It is preferred that the G-quartet is a parallel type. The number of G-quartets formed in the G-quartet-forming region (D) in the sensor of the present invention is not particularly limited, and can be, for example, one plane or two or more planes. It is preferred that the G-quartet-forming region (D) forms a guanine quadruplex (also referred to as G-quadruplex) in which G-quartets are stacked on top of each other. In the present invention, the sequence of the G-quartet-forming region (D) can be any sequence as long as it allows formation of the G-quartet. It is preferred that the G-quartet-forming region (D) has a sequence that allows formation of a guanine quadruplex.

The region that forms a G-quartet in the presence of porphyrin generates fluorescence when it forms a complex with porphyrin. According to the sensor of the present invention, the G-quartet-forming region (D) is inhibited from forming a G-quartet in the absence of a target and the inhibition of the formation of the G-quartet in the G-quartet-forming region (D) is cancelled due to the contact between the target and the binding region (A) and the G-quartet-forming region (D) forms a G-quartet in the presence of a target. Thus, according to the sensor of the present invention, in the absence of a target, since the G-quartet-forming region (D) cannot form a G-quartet, fluorescence owing to formation of a complex of the G-quartet-forming region (D) and porphyrin is not generated. On the other hand, according to the sensor of the present invention, in the presence of a target, G-quartet-forming region (D) forms a G-quartet and fluorescence owing to formation of a complex of the G-quartet-forming region (D) and porphyrin is generated. Therefore, for example, the presence or absence of a target in a sample or the amount of the target can be analyzed on the basis of the fluorescence generated by a complex of the G-quartet-forming region (D) and porphyrin.

As a nucleic acid molecule that forms the G-quartet, for example, a nucleic acid molecule (catalytic nucleic acid molecule) that generates a catalytic function of an enzyme is known. The catalytic function is not particularly limited and is, for example, the catalytic function of a redox reaction. The redox reaction is a reaction in which electrons are transferred between two substrates in a course of generating a product from the substrates, for example. The type of the redox reaction is not particularly limited. The catalytic function of the redox reaction can be, for example, activity similar to enzyme and specifically is, for example, activity similar to peroxidase (hereinafter referred to as "peroxidase-like activity"). The peroxidase activity can be, for example, horseradish peroxidase (HRP) activity. In the case where the catalytic nucleic acid molecule is a DNA sequence, it is commonly called DNA enzyme or DNAzyme. In the case where the catalytic nucleic acid molecule is an RNA sequence, it is commonly called RNA enzyme or RNAzyme. In the present invention, for example, such a catalytic nucleic acid molecule can be used as the G-quartet-forming region (D). Furthermore, in the present invention, the G-quartet-forming region (D) can be any region as long as it can form a G-quartet and, the presence or absence of the catalytic function is not limited.

Examples of the DNAzyme include the nucleic acid molecules disclosed in the following articles (1) to (4);

(1) Travascio et. al., Chem. Biol., 1998, vol. 5, pp. 505-517;
(2) Cheng et. al., Biochemistry, 2009, vol. 48, pp. 7817-7823;
(3) Teller et. al., Anal. Chem., 2009, vol. 81, pp. 9114-9119; and
(4) Tao et. al., Anal. Chem., 2009, vol. 81, pp. 2144-2149.

The G-quartet-forming region (D) may be, for example, a single-stranded nucleic acid molecule or a double-stranded nucleic acid molecule. The single-stranded nucleic acid molecule can form a G-quartet in a single-stranded G-quartet-forming region (D), for example. The double-stranded nucleic acid molecule includes a first region (D1) and a second region (D2), and a G-quartet can be formed by the first region (D1) and the second region (D2), for example. The latter double-stranded nucleic acid molecule can be, for example, a structure in which the first region and the second region are indirectly linked, which will be described specifically with reference to the nucleic acid molecule (IV) below.

The length of the single-stranded G-quartet-forming region (D) is not particularly limited. The lower limit of the length is, for example, 11-mer, 13-mer, or 15-mer. The upper limit of the length is, for example, 60-mer, 36-mer, or 18-mer.

In the double-stranded G-quartet-forming region (D), the lengths of the first region (D1) and the second region (D2) are not particularly limited. The length of the first region (D1) may be the same as or different from that of the second region (D2). The length of the first region (D1) is not particularly limited. The lower limit of the length is, for example, 7-mer, 8-mer, or 10-mer. The upper limit of the length is, for example, 30-mer, 20-mer, or 10-mer. The range of the length is, for example, from 7- to 30-mer, from 7- to 20-mer, or from 7- to 10-mer. The length of the second region (D2) is not particularly limited. The lower limit of the length is, for example, 7-mer, 8-mer, or 10-mer. The upper limit of the length is, for example, 30-mer, 20-mer, or 10-mer. The range of the length is, for example, from 7- to 30-mer, from 7- to 20-mer, or from 7- to 10-mer.

In the sensor of the present invention, the target is not particularly limited, and any target can be selected. Furthermore, a binding nucleic acid molecule that binds to a target can be used as the binding region (A) according to the selected target.

The target is not particularly limited, and examples thereof include low-molecular compounds, microorganisms, virus, food allergens, agricultural chemicals, mycotoxin, and antibodies. Examples of the low-molecular compound include melamine, antibiotics, agricultural chemicals, and endocrine-disrupting chemicals. Examples of the microorganisms include *Salmonella enterica, Listeria monocytogenes, Escherichia coli*, and mold. The virus can be, for example, norovirus.

The length of the binding region (A) is not particularly limited. The lower limit of the length is, for example, 12-mer, 15-mer, or 18-mer. The upper limit of the length is, for example, 140-mer, 80-mer, or 60-mer. The range of the length is, for example, from 12- to 140-mer, from 15- to 80-mer, or 18- to 60-mer.

In the present invention, "a sequence is complementary to another sequence" means that these are sequences between which annealing can be generated, for example. The annealing is also referred to as stem formation. With reference to "complementary to" in the present invention, the complementarity between two different sequences when they are aligned is, for example, at least 90%, at least 95%, at least 96%, at least 97%, at least 98%, at least 99%, or 100% (i.e., perfect complementation). Furthermore, "a sequence is complementary to another sequence in a nucleic acid molecule" means that bases of a sequence extending from its 5' side toward 3' side are complementary to bases of another sequence extending from its 3' side toward 5' side when they are compared.

The nucleic acid molecules (I), (II), (III), (IV), and (V) in the sensor of the present invention are described below. Each of the nucleic acid molecules can be described with reference to the description for other nucleic acid molecules, unless otherwise noted.

(1) Nucleic Acid Molecule (I)

The nucleic acid molecule (I) is a single-stranded nucleic acid molecule including the G-quartet-forming region (D), a blocking region (B), and the binding region (A) in this order. The blocking region (B) is complementary to a partial region (Dp) of the G-quartet-forming region (D), and a terminal region (Ab) of the binding region (A) on the blocking region (B) side is complementary to an adjacent region (Df) of the partial region (Dp) of the G-quartet-forming region (D) and is also complementary to a terminal region (Af) of the binding region (A) on the opposite side of the blocking region (B) side.

In the nucleic acid molecule (I), the G-quartet-forming region (D) is, for example, a single-stranded nucleic acid molecule.

The formation of a G-quartet in the G-quartet-forming region (D) in the nucleic acid molecule (I) is controlled to be switched-ON or switched-OFF depending on the presence or absence of a target on the basis of the following mechanism, for example. The present invention, however, is not limited to this mechanism. It is commonly considered that nucleic acid sequences are thermodynamically unstable between structures to be formed and the abundance ratio of the nucleic acid sequence of relatively high stability is high. Furthermore, it is commonly known that a binding nucleic acid molecule such as an aptamer changes into a more stable conformation due to the contact with a target in the presence of a target, whereby the binding nucleic acid molecule binds to the target. It is also commonly known that a nucleic acid molecule such as DNAzyme activates a catalytic activity by a stable conformation such as a G-quartet.

In the nucleic acid molecule (I), since the partial region (Dp) of the G-quartet-forming region (D) is complementary to the blocking region (B) and the adjacent region (Df) of the G-quartet-forming region (D) is complementary to the terminal region (Ab) of the binding region (A), a stem can be formed under these complementary relationships. Therefore, in the absence of a target, a stem of the partial region (Dp) of the G-quartet-forming region (D) and the blocking region (B) is formed and a stem of the adjacent region (Df) of the G-quartet-forming region (D) and the terminal region (Ab) of the binding region (A) is formed. The formation of the former stem inhibits formation of a G-quartet in the G-quartet-forming region (D), resulting in inhibition of formation of a complex of the G-quartet-forming region (D) and porphyrin (switched-OFF). The formation of the latter stem blocks formation of a more stable conformation in the binding region (A), thereby maintaining a blocking type structure in which the binding region (A) is not bound to a target. The molecule structure in this state is also called a blocking form or an inactive form. On the other hand, in the presence of a target, the binding region (A) changes into a more stable conformation due to the contact between the binding region (A) and the target. In accordance with this, the formation of a stem in the binding region (A) is released and the target binds to the binding region (A) which has changed into a more stable conformation by intramolecular annealing. Then, the formation of the stem in the G-quartet-forming region (D) is also released owing to formation of the conformation of the binding region (A) in accordance with the release of the formation of a stem in the binding region (A) so that the G-quartet-forming region (D) changes into a more stable conformation by intramolecular annealing, resulting in formation of a G-quartet within the region of the G-quartet-forming region (D). As a result, a complex of the G-quartet-forming region (D) and porphyrin is formed and fluorescence is generated by the complex (switched-ON). The structure in this state is also called an active form. Thus, according to the sensor of the present invention, since fluorescence owing to formation of the complex is not generated in the absence of a target and fluorescence owing to formation of the complex is generated only in the presence of a target, it is possible to perform target analysis such as qualitative analysis or quantitative analysis.

The nucleic acid molecule (I) may further include a stabilizing region (S). In this case, it is preferred that the G-quartet-forming region (D), the blocking region (B), the binding region (A), and the stabilizing region (S) are linked in this order. Hereinafter, in the case where the nucleic acid molecule (I) is described with reference to a single-stranded nucleic acid molecule including the stabilizing region (S), the stabilizing region (S) is optional and the nucleic acid molecule (I) may not include the stabilizing region (S).

The stabilizing region (S) is a sequence for stabilizing the structure when the binding region (A) binds to a target, for example. The stabilizing region (S) is complementary to the blocking region (B) or complementary to a part of the blocking region (B), for example. Specifically, it is preferred that the stabilizing region (S) is complementary to a terminal region (Ba) of the blocking region (B) on the binding region (A) side. In this case, for example, when a conformation of the binding region (A) is formed by intramolecular annealing in the presence of a target, a stem is also formed by the stabilizing region (S) linked to the binding region (A) and the terminal region (Ba) of the blocking region (B) linked to the binding region (A). The formation of such a stem in a region linked to the binding region (A) further stabilizes the conformation of the binding region (A) that binds to a target.

In the nucleic acid molecule (I), the order of the G-quartet-forming region (D), the blocking region (B), the binding region (A), and the optional stabilizing region (S) is not particularly limited, and, for example, they may be linked in this order from the 5' side or linked in this order from the 3' side, and the former is preferable. FIGS. 1A to 1C are schematic views showing, as an example of the nucleic acid molecule (I), a single-stranded nucleic acid molecule (I) in the state where the aforementioned regions are linked from the 5' side. FIG. 1A is a schematic view showing the order of the sequences. FIG. 1B is a schematic view of a blocking form in the absence of a target. FIG. 1C is a schematic view of an active form in the presence of a target. In FIGS. 1A to 1C, D indicates the building block (nucleotide) of the G-quartet-forming region (D), B indicates the building block of the blocking region (B), A indicates the building block of the binding region (A), and S indicates the building block of the stabilizing region (S). The lines among the building blocks indicate binding. FIGS. 1A to 1C schematically show the regions. The number of the building blocks (the length of the sequence) of each region is not particularly limited and the stabilizing region (S) is optional (hereinafter, the same applies).

As shown in FIG. 1A, an example of the nucleic acid molecule (I) includes the G-quartet-forming region (D), the blocking region (B), the binding region (A), and optionally the stabilizing region (S) in this order. In the nucleic acid molecule (I) in the absence of a target, for example, a part of the G-quartet-forming region (D) binds to the blocking region (B) and a part of the binding region (A) to form a stem, thereby forming a blocking type single-stranded nucleic acid molecule as shown in FIG. 1B. On the other hand, in the nucleic acid molecule (I) in the presence of a target, for example, the binding region (A) forms a conformation by intramolecular annealing due to the contact between the target and the binding region (A). In accordance with this, formation of a stem in the G-quartet-forming region (D) is released and the G-quartet-forming region (D) forms a G-quartet by the intramolecular annealing as shown in FIG. 1C. Furthermore, as shown in FIG. 1C, for example, binding between the blocking region (B) and the stabilizing region (S) makes the conformation of the binding region (A) further stable.

In the nucleic acid molecule (I), the G-quartet-forming region (D), the blocking region (B), the binding region (A), and optionally the stabilizing region (S) may be indirectly linked via spacer sequences, for example. However, it is preferred that the G-quartet-forming region (D), the blocking region (B), the binding region (A), and optionally the stabilizing region (S) are directly linked without involving the spacer sequence.

As described above, the G-quartet-forming region (D) includes a sequence complementary to the blocking region (B) and a sequence complementary to a part of the binding region (A). Also, as described above, the blocking region (B) is complementary to a part of the G-quartet-forming region (D) and is also complementary to the stabilizing region (S) if the nucleic acid molecule (I) includes the stabilizing region (S).

The sequence and the length of the blocking region (B) are not particularly limited, and can be determined appropriately according to the sequence and the length of the G-quartet-forming region (D), for example.

The length of the blocking region (B) is not particularly limited. The lower limit of the length is, for example, 1-mer, 2-mer, or 3-mer. The upper limit of the length is, for example, 20-mer, 15-mer, or 10-mer. The range of the length is, for example, from 1- to 20-mer, from 2- to 15-mer, or from 3- to 10-mer.

On the other hand, the length of the partial region (Dp) of the G-quartet-forming region (D) is as follows, for example. The lower limit of the length is, for example, 1-mer, 2-mer, or 3-mer. The upper limit of the length is, for example, 20-mer, 15-mer, or 10-mer. The range of the length is, for example, from 1- to 20-mer, from 2- to 15-mer, or from 3- to 10-mer. It is preferred that the length of the blocking region (B) is the same as that of the partial region (Dp) of the G-quartet-forming region (D), for example.

In the nucleic acid molecule (I), the position of the partial region (Dp) in the G-quartet-forming region (D), i.e., the region that anneals to the blocking region (B) in the G-quartet-forming region (D) is not particularly limited. In the case where the G-quartet-forming region (D), the blocking region (B), the binding region (A), and optionally the stabilizing region (S) are linked in this order, the partial region (Dp) can be set, for example, with the following conditions.

The length of the region (Db) between the blocking region (B) side end of the partial region (Dp) and the G-quartet-forming region (D) side end of the blocking region (B), which is an adjacent region of the partial region (Dp) in the G-quartet-forming region (D) is as follows. The lower limit of the length is, for example, 3-mer, 4-mer, or 5-mer. The upper limit of the length is, for example, 40-mer, 30-mer, or 20-mer. The range of the length is, for example, from 3- to 40-mer, from 4- to 30-mer, or from 5- to 20-mer.

The length of the region (Df) of the G-quartet-forming region (D) on the opposite side of the blocking region (B) side, which is an adjacent region of the partial region (Dp) is as follows. The lower limit of the length is, for example, 0-mer, 1-mer, or 2-mer. The upper limit of the length is, for example, 40-mer, 30-mer, or 20-mer. The range of the length is, for example, from 0- to 40-mer, 1- to 30-mer, or 2- to 20-mer.

As described above, the terminal region (Ab) of the binding region (A) on the blocking region (B) side is complementary to the adjacent region (Df) of the G-quartet-forming region (D). The terminal region (Ab) of the binding region (A) may be complementary to the entire region of the adjacent region (Df) of the G-quartet-forming region (D) or may be complementary to a partial region of the adjacent region (Df). In the latter case, it is preferred that the terminal region (Ab) of the binding region (A) is complementary to the terminal region of the adjacent region (Df) in the G-quartet-forming region (D) on the partial region (Dp) side.

The length of the terminal region (Ab) of the binding region (A), complementary to the adjacent region (Df) of the G-quartet-forming region (D) is not particularly limited. The lower limit of the length is, for example, 1-mer. The upper limit of the length is, for example, 20-mer, 8-mer, or 3-mer. The range of the length is, for example, from 1- to 20-mer, from 1- to 8-mer, or from 1- to 3-mer.

As described above, the stabilizing region (S) is complementary to the blocking region (B) or a part of the blocking region (B), for example. Specifically, it is preferred that the stabilizing region (S) is complementary to a terminal region (Ba) of the blocking region (B) on the binding region (A) side.

The sequence and the length of the stabilizing region (S) are not particularly limited. For example, the sequence and the length of the stabilizing region (S) can be determined according to the sequences and the lengths of the blocking region (B) and the binding region (A). The lower limit of the length of the stabilizing region (S) is, for example, 0-mer or 1-mer. The upper limit of the length is, for example, 10-mer, 5-mer, or 3-mer. The range of the length is, for example, from 0- to 10-mer, from 1- to 5-mer, or from 1- to 3-mer. On the other hand, for example, when the stabilizing region (S) is complementary to the entire blocking region (B), the length of the blocking region (B) is the same as that of the stabilizing region (S). Furthermore, for example, when the stabilizing region (S) is complementary to a part of the blocking region (B), the length of the part of the blocking region (B), e.g., the terminal region (Ba) is the same as that of the stabilizing region (S).

The full-length of the nucleic acid molecule (I) is not particularly limited. The lower limit of the length is, for example, 25-mer, 35-mer, or 40-mer. The upper limit of the length is, for example, 200-mer, 120-mer, or 80-mer. The range of the length is, for example, from 25- to 200-mer, from 35- to 120-mer, or from 40- to 80-mer.

The nucleic acid molecule (I) may further include a linker region(s) added to one end or both ends. Hereinafter, the linker region(s) added to the end(s) is also referred to as an additional linker region(s). The length of the additional linker region is not particularly limited and is, for example, in the range from 1- to 60-mer.

(2) Nucleic Acid Molecule (II)

The nucleic acid molecule (II) is a single-stranded nucleic acid molecule including the G-quartet-forming region (D), a blocking region (B), the binding region (A), and a stabilizing region (S) in this order. The blocking region (B) is complementary to a partial region (Dp) of the G-quartet-forming region (D), and a terminal region (Ba) of the blocking region (B) on a binding region (A) side is complementary to the stabilizing region (S).

In the nucleic acid molecule (II), the G-quartet-forming region (D) is, for example, a single-stranded nucleic acid molecule.

In the nucleic acid molecule (II), it is preferred that the binding region (A) has a sequence that alone does not allow intramolecular annealing required for binding to a target. Furthermore, in the nucleic acid molecule (II), it is preferred that the binding region (A), the terminal region (Ba), and the stabilizing region (S) as a whole form the conformation by annealing of the terminal region (Ba) of the blocking region (B) adjacent to the binding region (A) and the stabilizing region (S) in the presence of a target.

The formation of a G-quartet in the G-quartet-forming region (D) in the nucleic acid molecule (II) is controlled to be switched-ON or switched-OFF depending on the presence or absence of a target on the basis of the following mechanism, for example. The present invention, however, is not limited to this mechanism.

In the single-stranded nucleic acid (II), since the partial region (Dp) of the G-quartet-forming region (D) is complementary to the blocking region (B), a stem can be formed under these complementary relationships. Therefore, in the absence of a target, a stem of the partial region (Dp) of the G-quartet-forming region (D) and the blocking region (B) is formed. The formation of this stem inhibits formation of a G-quartet in the G-quartet-forming region (D), resulting in inhibition of formation of a complex of the G-quartet-forming region (D) and porphyrin (switched-OFF). Furthermore, since the binding region (A) has a sequence that alone does not allow intramolecular annealing required for binding to a target, formation of a more stable conformation for binding to the target is blocked, thereby maintaining a state where the binding region (A) is not bound to a target. That is, in the absence of a target, the nucleic acid molecule (II) maintains a blocking type structure. The molecule structure in this state is also called a blocking form or an inactive form. On the other hand, in the presence of a target, the binding region (A) changes into a more stable conformation due to the contact between the binding region (A) and the target. In accordance with this, the formation of a stem of the terminal region (Ba) of the blocking region (B) and the partial region (Dp) of the G-quartet-forming region (D) is released and a stem is newly formed by annealing of the terminal region (Ba) of the blocking region (B) and the stabilizing region (S). This stem takes a role of performing intramolecular annealing required for binding the binding region (A) to a target, the stem and the binding region (A) as a whole form the conformation, and the target binds to the binding region (A). Then, owing to release of the formation of the stem of the blocking region (B) and the G-quartet-forming region (D), the G-quartet-forming region (D) newly forms a G-quartet by intramolecular annealing, resulting in formation of a complex of the G-quartet-forming region (D) and porphyrin, thereby generating fluorescence (switched-ON). The structure in this state is also called an active form. Thus, according to the sensor of the present invention, since fluorescence owing to formation of the complex is not generated in the absence of a target and fluorescence owing to formation of the complex is generated only in the presence of a target, it is possible to perform target analysis such as qualitative analysis or quantitative analysis.

Figure 2:
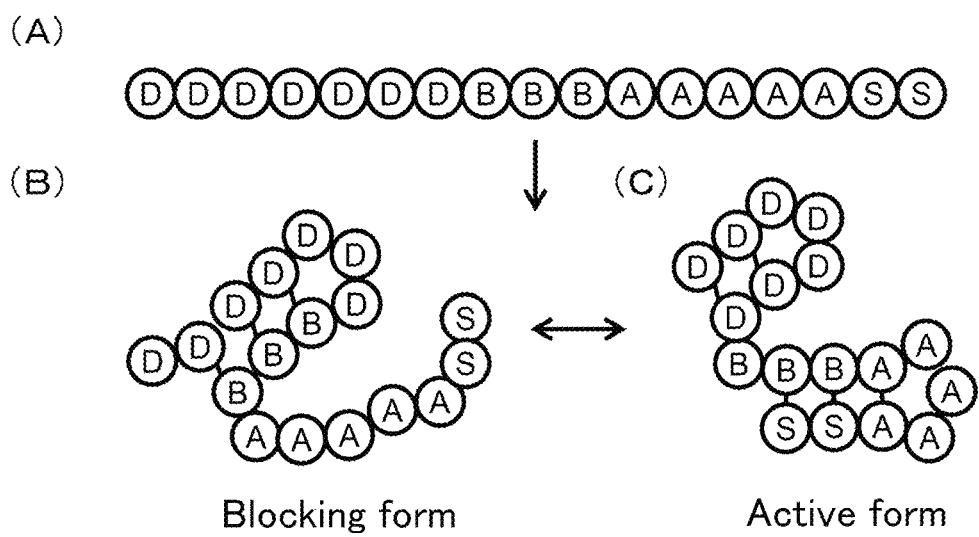
FIGS. 2A to 2C are schematic views showing another example of a nucleic acid molecule in the sensor of the present invention.

In the nucleic acid molecule (II), the order of the G-quartet-forming region (D), the blocking region (B), the binding region (A), and the stabilizing region (S) is not particularly limited, and, for example, they may be linked in this order from the 5' side or linked in this order from the 3' side, and the former is preferable. FIGS. 2A to 2C are schematic views showing, as an example of the nucleic acid molecule (II), a single-stranded nucleic acid molecule (I) in the state where the aforementioned regions are linked from the 5' side. FIG. 2A is a schematic view showing the order of the regions. FIG. 2B is a schematic view of a blocking form in the absence of a target. FIG. 2C is a schematic view of an active form in the presence of a target. In FIGS. 2A to 2C, D indicates the building block (nucleotide) of the G-quartet-forming region (D), B indicates the building block of the blocking region (B), A indicates the building block of the binding region (A), and S indicates the building block of the stabilizing region (S). The lines among the building blocks indicate binding. FIGS. 2A to 2C schematically show the regions. The number of the building blocks (the length of the sequence) of each region is not particularly limited (hereinafter, the same applies).

As shown in FIG. 2A, an example of the nucleic acid molecule (II) includes the G-quartet-forming region (D), the blocking region (B), the binding region (A), and the stabilizing region (S) in this order. In the nucleic acid molecule (II) in the absence of a target, for example, a part of the G-quartet-forming region (D) binds to the blocking region (B) to form a stem, thereby forming a blocking type single-stranded nucleic acid as shown in FIG. 2B. At this moment, the binding region (A) does not form the conformation. On the other hand, in the nucleic acid molecule (II) in the presence of a target, for example, formation of a stem of the blocking region (B) and the G-quartet-forming region (D) is released due to the contact between the target and the binding region (A), a stem is newly formed by the blocking region (B) and the stabilizing region (S), whereby the binding region (A), the blocking region (B), and the stabilizing region (S) form a conformation as shown in FIG. 2C. Furthermore, for example, in accordance with the release of the formation of the stem of the blocking region (B) and the G-quartet-forming region (D), the G-quartet-forming region (D) forms a G-quartet by intramolecular annealing. Moreover, as shown in FIG. 2C, for example, binding between the blocking region (B) and the stabilizing region (S) makes the conformation formed of the binding region (A), the blocking region (B), and the stabilizing region (S) further stable.

The description for the nucleic acid molecule (I) can be applied to the nucleic acid molecule (II), unless otherwise noted. In the nucleic acid molecule (II), the G-quartet-forming region (D), the blocking region (B), and the stabilizing region (S) are the same as those described for the nucleic acid molecule (I), for example.

As described above, the blocking region (B) includes a sequence complementary to the G-quartet-forming region (D) and a sequence complementary to the stabilizing region (S). Specifically, the blocking region (B) is complementary to the partial region (Dp) of the G-quartet-forming region (D), and the terminal region (Ba) of the blocking region (B) on the binding region (A) side is complementary to the stabilizing region (S).

In the blocking region (B), the length of the terminal region (Ba) complementary to the stabilizing region (S) is not particularly limited. The lower limit of the length is, for example, 1-mer. The upper limit of the length is, for example, 15-mer, 10-mer, or 3-mer. The range of the length is, for example, from 1- to 10-mer, from 1- to 5-mer, or from 1- to 3-mer.

The full-length of the nucleic acid molecule (II) is not particularly limited. The lower limit of the length is, for example, 25-mer, 35-mer, or 40-mer. The upper limit of the length is, for example, 200-mer, 120-mer, or 80-mer. The range of the length is, for example, from 25- to 200-mer, from 35- to 120-mer, or 40- to 80-mer.

(3) Nucleic Acid Molecule (III)

The nucleic acid molecule (III) is a single-stranded nucleic acid molecule including the G-quartet-forming region (D), a stem-forming region ($S_D$), the binding region (A), and a stem-forming region ($S_A$). The stem-forming region ($S_D$) includes a sequence complementary to the G-quartet-forming region (D) and the stem-forming region ($S_A$) includes a sequence complementary to the binding region (A).

In the nucleic acid molecule (III), the G-quartet-forming region (D) is, for example, a single-stranded nucleic acid molecule.

The formation of a G-quartet in the G-quartet-forming region (D) in the nucleic acid molecule (III) is controlled to be switched-ON or switched-OFF depending on the presence or absence of a target on the basis of the following mechanism, for example. The present invention, however, is not limited to this mechanism. In the nucleic acid molecule (III) in the absence of a target, formation of a G-quartet in the G-quartet-forming region (D) is inhibited by annealing of the G-quartet-forming region (D) and the stem-forming region ($S_D$) within the molecule, resulting in inhibition of formation of a complex of the G-quartet-forming region (D) and porphyrin (switched-OFF). Furthermore, the structure of the binding region (A) is immobilized by annealing of the binding region (A) and the stem-forming region ($S_A$) within the molecule. The molecule structure in this state is also called an inactive form. On the other hand, in the nucleic acid molecule (III) in the presence of a target, the annealing of the binding region (A) and the stem-forming region ($S_A$) is released due to the contact between the target and the binding region (A), and the conformation of the binding region (A) changes into a more stable conformation. In accordance with this, the annealing of the G-quartet-forming region (D) and the stem-forming region ($S_D$) is released and a G-quartet is formed within the region of the G-quartet-forming region (D), resulting in formation of a complex of the G-quartet-forming region (D) and porphyrin, thereby generating fluorescence (switched-ON). The molecule structure in this state is also called an active form. Thus, according to the nucleic acid molecule (III), since fluorescence owing to formation of the complex is not generated in the absence of a target and fluorescence owing to formation of the complex is generated only in the presence of a target, it is possible to perform target analysis such as qualitative analysis or quantitative analysis.

It is preferred that the whole or a part of the stem-forming region ($S_D$) has a sequence complementary to a part of the G-quartet-forming region (D), for example. It is also preferred that the whole or a part of the stem-forming region ($S_A$) has a sequence complementary to a part of the binding region (A), for example.

In the nucleic acid molecule (III), the order of the regions can be any order as long as it allows the annealing of the G-quartet-forming region (D) and the stem-forming region ($S_D$) and the annealing of the binding region (A) and the stem-forming region ($S_A$) within the molecule. Specific examples of the order of the regions are as follows.

(1) 5'-A-$S_D$-D-$S_A$-3'
(2) 5'-$S_A$-D-$S_D$-A-3'
(3) 5'-D-$S_A$-A-$S_D$-3'
(4) 5'-$S_D$-A-$S_A$-D-3'

In the aforementioned forms (1) to (4), switching-ON and switching-OFF of formation of a G-quartet is performed as follows, for example. In the absence of a target, the binding nucleic acid molecule (A) and the stem-forming region ($S_A$) form a stem and the G-quartet-forming molecule (D) and the stem-forming region ($S_D$) form a stem, thereby inhibiting formation of a G-quartet in the G-quartet-forming molecule (D). In the presence of a target, the formation of each stem is released due to the contact between the target and the binding nucleic acid molecule (A), thereby forming a G-quartet in the G-quartet-forming molecule (D).

In the forms (1) and (3), it is preferred that the stem-forming region ($S_D$) is complementary to the 3' side region of the G-quartet-forming molecule (D) and the stem-forming region ($S_A$) is complementary to the 3' side region of the binding nucleic acid molecule (A). In the forms (2) and (4), it is preferred that the stem-forming region ($S_D$) is complementary to the 5' side region of the G-quartet-forming molecule (D) and the stem-forming region ($S_A$) is complementary to the 5' side region of the binding nucleic acid molecule (A).

In the nucleic acid molecule (III), for example, the regions may be linked directly or indirectly. The direct link means that the 3' end of one region and the 5' end of the other region are bound directly, for example. The indirect link means that the 3' end of one region and the 5' end of the other region are bound via an intervening linker region, for example. The intervening linker region may be, for example, a nucleic acid sequence or a non-nucleic acid sequence, and the former is preferable.

It is preferred that the nucleic acid molecule (III) includes two intervening linker regions not complementary to each other as the intervening linker regions, for example. The positions of the two intervening linker regions are not particularly limited.

Specific examples of the order of regions in the case where the forms (1) to (4) each further includes two intervening linker region are as follows. In the following examples, an intervening linker region that links to the binding nucleic acid molecule (A) is indicated by ($L_1$) and an intervening linker region that links to the G-quartet-forming molecule (D) is indicated by ($L_2$). The nucleic acid molecule (II) may include both of the ($L_1$) and ($L_2$) or either one of the ($L_1$) and ($L_2$) as the intervening linker region, for example.

(1') 5'-A-$L_1$-$S_D$-D-$L_2$-$S_A$-3'
(2') 5'-$S_A$-$L_2$-D-$S_D$-$L_1$-A-3'
(3') 5'-D-$L_2$-$S_A$-A-$L_1$-$S_D$-3'
(4') 5'-$S_1$-$L_1$-A-$S_A$-$L_2$-D-3'

In the forms (1') to (4'), switching-ON and switching-OFF of formation of a G-quartet is performed as follows, for example. In the absence of a target, for example, the binding nucleic acid molecule (A) and the stem-forming region ($S_A$) form a stem and the G-quartet-forming molecule (D) and the stem-forming region ($S_D$) form a stem, and the intervening linker region ($L_1$) and the intervening linker region ($L_2$) form an internal loop between these two stems, thereby inhibiting formation of a G-quartet in the G-quartet-forming molecule (D). In the presence of a target, the formation of each stem is released due to the contact between the target and the binding nucleic acid molecule (A), whereby a G-quartet is formed in the G-quartet-forming molecule (D).

Figure 3A:
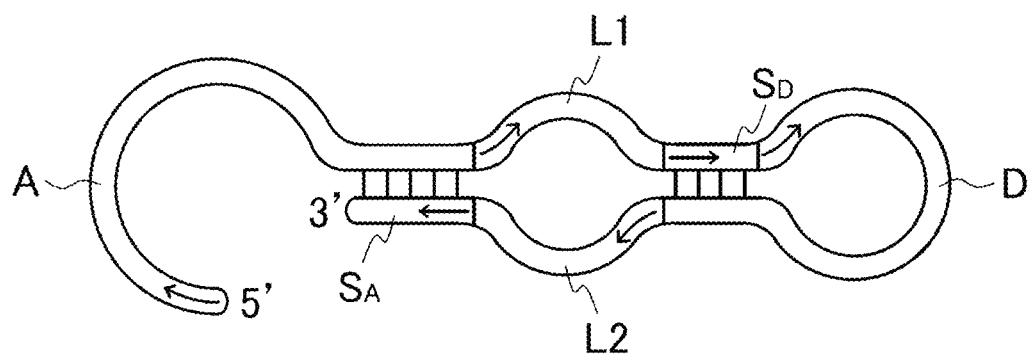
FIGS. 3A and 3B are schematic views showing still another example of a nucleic acid molecule in the sensor of the present invention.
Figure 3B:
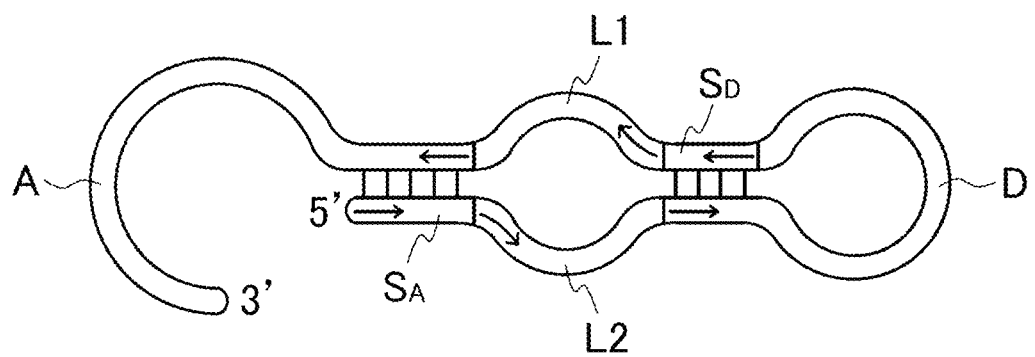
Figure 4A:
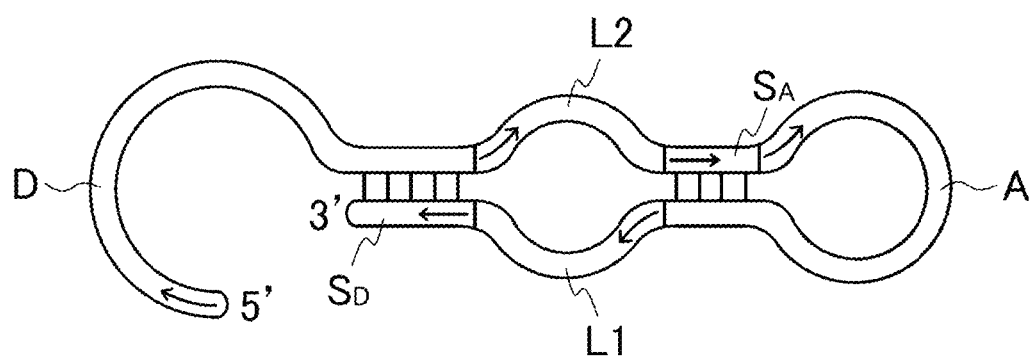
FIGS. 4A and 4B are schematic views showing still another example of a nucleic acid molecule in the sensor of the present invention.
Figure 4B:
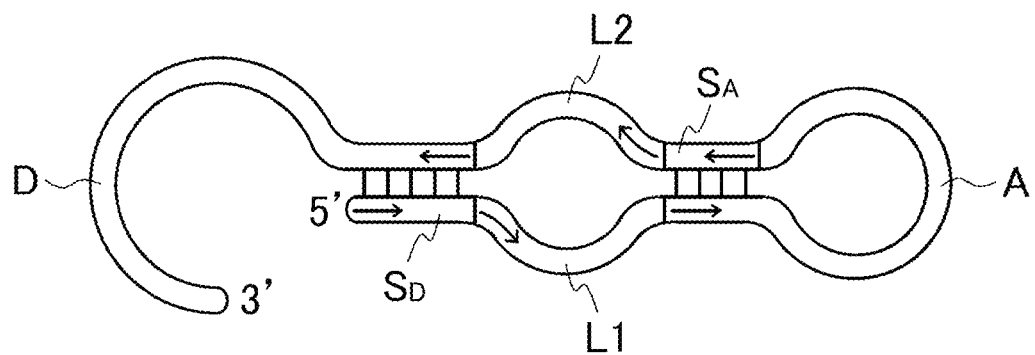

With reference to the forms (1') to (4'), examples of the state of the nucleic acid molecule (III) in the absence of a target are shown in FIGS. 3A and 3B and FIGS. 4A and 4B. The order of the regions in the nucleic acid molecule (III) shown in FIG. 3A and the order of the regions in the nucleic acid molecule (III) shown in FIG. 3B are in reverse, and the order of the regions in the nucleic acid molecule (III) shown in FIG. 4A and the order of the regions in the nucleic acid molecule (III) shown in FIG. 4B are in reverse. FIG. 3A shows the form (1'), FIG. 3B shows the form (2'), FIG. 4A shows the form (3'), and FIG. 4B shows the form (4').

In FIGS. 3A and 3B and FIGS. 4A and 4B, A indicates the binding nucleic acid molecule (A), L1 indicates the intervening linker region (L1), $S_D$ indicates the stem-forming sequence ($S_D$), D indicates the G-quartet-forming molecule (D), L2 indicates the intervening linker region (L2), and $S_A$ indicates the stem-forming sequence ($S_A$). As shown in FIGS. 3A and 3B and FIGS. 4A and 4B, in the absence of a target, stems are formed at two positions by self annealing of the nucleic acid molecule (II) and an internal loop is formed between the stems. Furthermore, in the presence of a target, the formation of the two stems are released due to the binding between the target and the binding nucleic acid molecule (A), resulting in formation of a G-quartet in the G-quartet-forming molecule (D) and formation of a complex of the G-quartet-forming molecule (D) and porphyrin, thereby generating fluorescence.

In the nucleic acid molecule (III), the lengths of the stem-forming sequence ($S_A$) and the stem-forming sequence ($S_D$) are not particularly limited. The length of the stem-forming sequence ($S_A$) is, for example, from 1- to 60-mer, from 1- to 10-mer, or from 1- to 7-mer. The length of the stem-forming sequence ($S_D$) is, for example, from 1- to 30-mer, from 0- to 10-mer, from 1- to 10-mer, from 0- to 7-mer, or from 1- to 7-mer. The length of the stem-forming sequence ($S_A$) may be, for example, the same as that of the stem-forming sequence ($S_D$), or the former may be longer than the latter or vice versa.

The lengths of the intervening linker regions ($L_1$) and ($L_2$) are not particularly limited. The length of each of the intervening linker regions ($L_1$) and ($L_2$) is, for example, from 0- to 30-mer, from 1- to 30-mer, from 1- to 15-mer, or from 1- to 6-mer. The length of the intervening linker region ($L_1$) may be the same as or different from that of the intervening linker region ($L_2$), for example. In the latter case, the difference between the length of the intervening linker region ($L_1$) and the length of the intervening linker region ($L_2$) is not particularly limited, and is, for example, from 1- to 10-mer, 1- or 2-mer, or 1-mer.

The length of the nucleic acid molecule (III) is not particularly limited. The length of the nucleic acid molecule (II) is, for example, from 40- to 120-mer, from 45- to 100-mer, or from 50- to 80-mer.

The single-stranded nucleic acid molecule (III) may further include the additional linker region(s) at one end or both ends. The length of the additional linker region is not particularly limited and is, for example, as described above.

One end of the nucleic acid molecule (III) may be linked to a base material via the additional linker region, for example.

(4) Nucleic Acid Molecule (IV)

The nucleic acid molecule (IV) is a single-stranded nucleic acid molecule including the G-quartet-forming region (D) and the binding region (A). The G-quartet-forming region (D) includes a first region (D1) and a second region (D2) that form a G-quartet. The first region (D1) is located on one end side of the binding region (A) and the second region (D2) is located on the other end side of the binding region (A).

In the nucleic acid molecule (IV), the G-quartet-forming region (D) is, for example, a double-stranded type (hereinafter, also referred to as a "split type"). The split type G-quartet-forming molecule (D) is a molecule including the first region (D1) and the second region (D2) that form a G-quartet in pairs. In the nucleic acid molecule (IV), the first region (D1) and the second region (D2) can have any sequence as long as they form a G-quartet. It is preferred that the first region (D1) and the second region (D2) have sequences that form a guanine quadruplex.

The formation of a G-quartet in the G-quartet-forming region (D) in the nucleic acid molecule (IV) is controlled to be switched-ON or switched-OFF depending on the presence or absence of a target on the basis of the following mechanism, for example. The present invention, however, is not limited to this mechanism. As described above, in the nucleic acid molecule (IV), the first region (D1) and the second region (D2) that form a G-quartet in pairs are disposed at a distance via the binding region (A). Since the first region (D1) and the second region (D2) are disposed at a distance in this manner, formation of a G-quartet of the first region (D1) and the second region (D2) is inhibited in the absence of a target, resulting in inhibition of formation of a complex of the G-quartet-forming molecule (D) and porphyrin (switched-OFF). The molecule structure in this state is also called an inactive form. On the other hand, in the nucleic acid molecule (IV) in the presence of a target, the conformation of the binding region (A) changes into a more stable conformation having a stem loop structure due to the contact between the target and the binding region (A). In accordance with this change of the conformation of the binding region (A), the first region (D1) and the second region (D2) come close to each other to form a G-quartet, resulting in formation of a complex of the G-quartet-forming region (D) and porphyrin, thereby generating fluorescence (switched-ON). The molecule structure in this state is also called an active form. Thus, according to the nucleic acid molecule (IV), since fluorescence owing to formation of the complex is not generated in the absence of a target and fluorescence owing to formation of the complex is generated only in the presence of a target, it is possible to perform target analysis such as qualitative analysis or quantitative analysis.

As described above, the nucleic acid molecule (IV) employs a double-stranded nucleic acid molecule as the G-quartet-forming region (D), and the first region (D1) and the second region (D2) are disposed via the binding region (A). Thus, for example, there is no need to set conditions by the type of an aptamer so that a desired aptamer can be set as the binding region (A). Therefore, the nucleic acid molecule (IV) is superior in general versatility.

In the nucleic acid molecule (IV), the first region (D1) and the second region (D2) can be disposed in any way as long as they are disposed via the binding region (A). Either the first region (D1) or the second region (D2) may be disposed at the 5' side or the 3' side of the binding region (A). Hereinafter, for the sake of convenience, the nucleic acid molecule (IV) will be described with reference to an example in which the first region (D1) is disposed at the 5' side of the binding region (A) and the second region (D2) is disposed at the 3' side of the binding region (A) unless otherwise stated.

In the nucleic acid molecule (IV), for example, the first region (D1) and the binding region (A) may be linked directly or indirectly and the second region (D2) and the binding region (A) may be linked directly or indirectly. The direct link means that the 3' end of the one region and the 5' end of the other region are bound directly, for example. The indirect link means that the 3' end of the one region and the 5' end of the other region are bound via the intervening linker region, for example. Specifically, it means that the 3' end of the one region and the 5' end of the intervening linker region is bound directly and the 3' end of the intervening linker region and the 5' end of the other region are bound directly. The intervening linker region may be, for example, a nucleic acid sequence or a non-nucleic acid sequence, and the former is preferable.

As described above, it is preferred that the nucleic acid molecule (IV) includes the intervening linker region (first linker region (L1)) between the first region (D1) and the binding region (A) and includes the intervening linker region (second linker region (L2)) between the second region (D2) and the binding region (A). The nucleic acid molecule (IV) may include either one of the first linker region (L1) and the second linker region (L2) and preferably includes both of them. In the case where the nucleic acid molecule (IV) includes both of the first linker region (L1) and the second linker region (L2), the lengths of them may be identical to or different from each other.

The length of the linker region is not particularly limited. The lower limit of the length is, for example, 1-mer, 3-mer, 5-mer, 7-mer, or 9-mer. The upper limit of the length is, for example, 20-mer, 15-mer, or 10-mer.

It is preferred that the base sequence of the first linker region (L1) from the 5' end side and the base sequence of the second linker region (L2) from the 3' end side are not complementary to each other, for example. In this case, the base sequence of the first linker region (L1) from the 5' end side and the base sequence of the second linker region (L2) from the 3' end side in an aligned state can be said to be a region that forms an internal loop within the molecule of the nucleic acid molecule (IV). When the nucleic acid molecule (IV) includes the first linker region (L1) and the second linker region (D2), which are not complementary to each other, between the first region (D1) and the binding region (A) and between the second region (D2) and the binding region (A), respectively, the distance between the first region (D1) and the second region (D2) can be kept sufficiently, for example. Thus, for example, it is possible to sufficiently suppress formation of a G-quartet of the first region (D1) and the second region (D2) in the absence of a target and to sufficiently reduce the background based on generation of fluorescence in the absence of a target.

Figure 5:
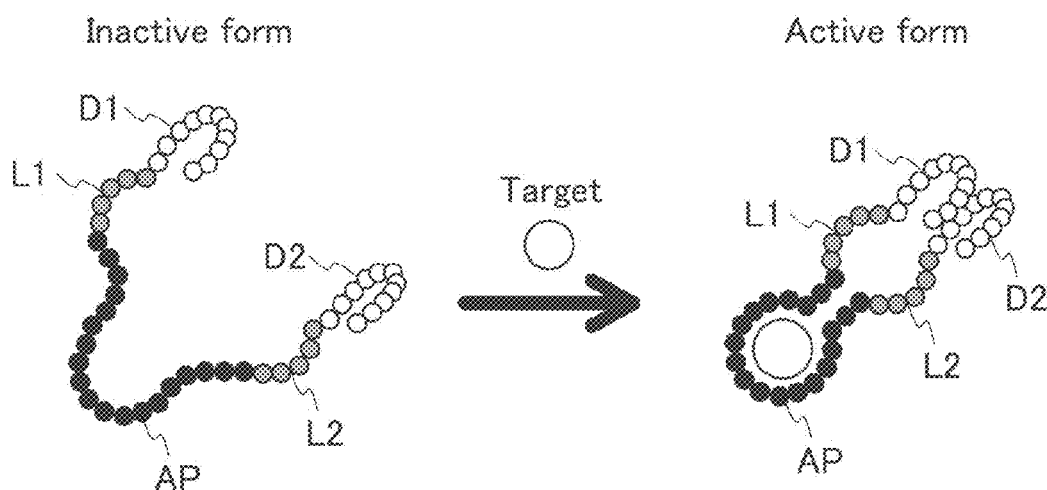
FIG. 5 is a schematic view showing still another example of a nucleic acid molecule in the sensor of the present invention.

With reference to the nucleic acid molecule (IV) including the first linker region (L1) and the second linker region (L2), switching-ON and switching-OFF of generation of fluorescence by the first region (D1) and the second region (D2) will be described using the schematic view of FIG. 5. However, the present invention is not limited thereto. FIG. 5 is a schematic view showing switching-ON and switching-OFF of generation of fluorescence in the nucleic acid molecule (IV). As shown in the left diagram in FIG. 5, in the absence of a target, the nucleic acid molecule (IV) takes an inactive form in which formation of a G-quartet of the first region (D1) and the second region (D2) is suppressed. On the other hand, in the presence of a target, the conformation of the binding region (A) changes due to the contact between the target and the binding region (A). In accordance with this, the first region (D1) and the second region (D2) come close to each other and the nucleic acid molecule (IV) takes an active form in which the first region (D1) and the second region (D2) form a G-quartet.

In the case where the nucleic acid molecule (IV) is represented by "D1-W-D2" and includes only the first linker region (L1) as a linker, for example, W in the formula includes the first linker region (L1) and the binding region (A) in this order from the 5' side, for example. Furthermore, in the case where the nucleic acid molecule (IV) includes only the second linker region (L2), for example, W in the formula includes the binding region (A) and the second linker region (L2) in this order from the 5' side, for example. Moreover, in the case where the nucleic acid molecule (IV) includes both of the first linker region (L1) and the second linker region (L2), W in the formula includes the first linker region (L1), the binding region (A), and the second linker region (L2) in this order from the 5' side, for example. In this case, the nucleic acid molecule (IV) represented by "D1-W-D2" can also be represented by "D1-L1-A-D2", "D1-A-L2-D2", or "D1-L1-A-L2-D2".

In the nucleic acid molecule (IV), it is preferred that the first region (D1) and the second region (D2) include sequences complementary to each other at the ends on the opposite side of the position of the binding region (A), for example. Specifically, for example, in the case where the first region (D1) is disposed on the 5' side of the binding region (A), it is preferred that the first region (D1) and the second region (D2) include sequences complementary to each other at the 5' end of the first region (D1) and the 3' end of the second region (D2), respectively. Furthermore, for example, in the case where the first region (D1) is disposed on the 3' side of the binding region (A), it is preferred that the first region (D1) and the second region (D2) include sequences complementary to each other at the 3' end of the first region (D1) and the 5' end of the second region (D2), respectively. When the first region (D1) and the second region (D2) include sequences complementary to each other at their ends in this manner, it is possible to form a stem structure of these sequences by intramolecular annealing. Therefore, for example, in the presence of a target, when the first region (D1) and the second region (D2) come close to each other in accordance with the change of the conformation of the binding region (A) due to the contact between the target and the binding region (A), it becomes easier to form a G-quartet of the first region (D1) and the second region (D2) owing to formation of a stem structure of the sequences.

The nucleic acid molecule (IV) can be represented, for example, by "D1-W-D2" as described above. Specifically, the nucleic acid molecule (IV) can be represented by the following formula (I).

[Chemical formula I]

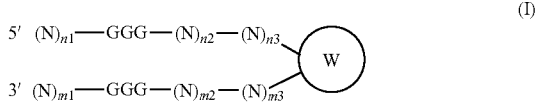

(I)

In the formula (I), the sequence $(N)_{n1}$-GGG-$(N)_{n2}$-$(N)_{n3}$- on the 5' side is the sequence (d1) of the first region (D1) and the sequence —$(N)_{m3}$-$(N)_{m2}$-GGG-$(N)_{m1}$ on the 3' side is the sequence (d2) of the second region (D2). W indicates a region between the first region (D1) and the second region (D2), which includes the binding region (A). N indicates bases, and n1, n2, n3, m1, m2, and m3 indicate the repeated numbers of bases N.

Although the formula (I) shows the state of intermolecular alignment of the first region (D1) and the second region (D2) in the nucleic acid molecule (IV), this is a schematic view for showing the relationship between the sequence of the first region (D1) and the sequence of the second region (D2). In the present invention, the first region (D1) and the second region (D2) are not limited to this state.

In the sequence (d1) of the first region (D1) and the sequence (d2) of the second region (D2), it is preferred that $(N)_{n1}$ and $(N)_{m1}$ satisfy the following condition (1), $(N)_{n2}$ and $(N)_{m2}$ satisfy the following condition (2), and $(N)_{n3}$ and $(N)_{m3}$ satisfy the following condition (3), for example.

Condition (1)

In $(N)_{n1}$ and $(N)_{m1}$, the base sequence of $(N)_{n1}$ from the 5' end side is complementary to the base sequence of $(N)_{m1}$ from the 3' end side, and n1 and m1 are both 0 or the same positive integers.

Condition (2)

In $(N)_{n2}$ and $(N)_{m2}$, the base sequence of $(N)_{n2}$ from the 5' end side is not complementary to the base sequence of $(N)_{m2}$ from the 3' end side, and n2 and m2 are positive integers and may be identical to or different from each other.

Condition (3)

In $(N)_{n3}$ and $(N)_{m3}$, n3 and m3 each are 3 or 4 and may be identical to or different from each other, and $(N)_{n3}$ and $(N)_{m3}$ each include three G bases. In the case where n3 or m3 is 4, the second or the third base of each of $(N)_{n3}$ and $(N)_{m3}$ is base H which is the base other than G.

The condition (1) is a condition of $(N)_{n1}$ at the 5' end and $(N)_{m1}$ at the 3' end in the case where the first region (D1) and the second region (D2) are aligned. In the condition (1), the base sequence of $(N)_{n1}$ from the 5' end side and the base sequence of $(N)_{m1}$ from the 3' end side are complementary to each other and are of the same length. Since $(N)_{n1}$ and $(N)_{m1}$ have the sequences of the same length complementary to each other, $(N)_{n1}$ and $(N)_{m1}$ can be said to be a stem region that forms a stem in an aligned state.

n1 and m1 are simply required to be both 0 or the same positive integers. For example, n1 and m1 each are 0, 1 to 10, 1, 2, or 3.

The condition (2) is a condition of $(N)_{n2}$ and $(N)_{m2}$ in the case where the first region (D1) and the second region (D2) are aligned. In the condition (2), the base sequence of $(N)_{n2}$ and the base sequence of $(N)_{m2}$ are not complementary to each other, and the lengths of n2 and m2 may be identical to or different from each other. Since $(N)_{n2}$ and $(N)_{m2}$ are sequences not complementary to each other, $(N)_{n2}$ and $(N)_{m2}$ can be said to be a region that forms an internal loop in an aligned state.

n2 and m2 are positive integers, and each are 1 to 10, 1, or 2, for example. n2 and m2 may be identical to or different from each other. n2 and m2 may satisfy, for example, any of n2=m2, n2>m2, and n2<m2 and are preferably satisfy n2>m2 or n2<m2.

The condition (3) is a condition of $(N)_{n3}$ and $(N)_{m3}$ in the case where the first region (D1) and the second region (D2) are aligned. In the condition (3), the base sequence of $(N)_{n3}$ and the base sequence of $(N)_{m3}$ each are a 3-mer or 4-mer sequence including three G bases and may be identical to or different from each other. In the case where n3 or m3 is 4, the second or the third base of each of $(N)_{n3}$ and $(N)_{m3}$ is base H which is the base other than G. Each of $(N)_{n3}$ and $(N)_{m3}$ including three G is a G region that forms a G-quartet with GGG between $(N)_{n1}$ and $(N)_{n2}$ and GGG between $(N)_{m1}$ and $(N)_{m2}$.

n3 and m3 may satisfy, for example, any of n3=m3, n3>m3, and n3<m3, and are preferably satisfy n3>m3 or n3<m3.

The base H which is the base other than G can be A, C, T, or U. The base H is preferably A, C, or T.

Specific examples of the condition (3) include the following conditions (3-1), (3-2), and (3-3).

Condition (3-1)

The sequence of one of $(N)_{n3}$ and $(N)_{m3}$ from the 5' side is GHGG and the sequence of the other of $(N)_{n3}$ and $(N)_{m3}$ from the 5' side is GGG.

Condition (3-2)

The sequence of one of $(N)_{n3}$ and $(N)_{m3}$ from the 5' side is GGHG and the sequence of the other of $(N)_{n3}$ and $(N)_{m3}$ from the 5' side is GGG.

Condition (3-3)

Each of the sequences of $(N)_{n3}$ and $(N)_{m3}$ is GGG.

The length of the first region (D1) is not particularly limited. The lower limit of the length is, for example, 7-mer, 8-mer, or 10-mer. The upper limit of the length is, for example, 30-mer, 20-mer, or 10-mer. The range of the length is, for example, from 7- to 30-mer, from 1- to 20-mer, or from 7- to 10-mer. The length of the second region (D2) is not particularly limited. The lower limit of the length is, for example, 7-mer, 8-mer, or 10-mer. The upper limit of the length is, for example, 30-mer, 20-mer, or 10-mer. The range of the length is, for example, from 7- to 30-mer, from 7- to 20-mer, or from 7- to 10-mer. The lengths of the first region (D1) and the second region (D2) may be identical to or different from each other.

Examples of the combination of the sequence (d1) of the first region (D1) and the sequence (d2) of the second region (D2) in the nucleic acid molecule (IV) are shown below. However, the present invention is not limited thereto. In each of the following combinations 1 to 49, W indicates a region between the sequence (d1) and the sequence (d2) in the nucleic acid molecule (IV), regions written in lower cases on the 5' end side and the 3' end side respectively indicate $(N)_{n1}$ and $(N)_{m1}$, underlined regions on the 5' end side and the 3' end side respectively indicate $(N)_{n2}$ and $(N)_{m2}$, and regions between W and the underlined regions on the 5' end side and the 3' end side respectively indicate $(N)_{n3}$ and $(N)_{m3}$.

TABLE 1

| Sequence Name | combination SEQ ID NO: | Sequence 5'- d1         d2 -3' |
|---|---|---|
| dsGs0028 | 1 | tcaGGGACGGG-W-GTGGAGGGtga |
| dsGs0025 | 2 | acaGGGACGGG-W-GTGGAGGGtgt |
| dsGs0022 | 3 | caaGGGACGGG-W-GTGGAGGGttg |
| dsGs0026 | 4 | ccaGGGACGGG-W-GTGGAGGGtgg |
| dsGs0006 | 5 | caGGGACGGG-W-GTGGAGGGtg |
| dsGs0038 | 6 | cacGGGACGGG-W-GTGGAGGGGtg |
| dsGs0027 | 7 | gcaGGGACGGG-W-GTGGAGGGtgc |
| dsGs0005 | 8 | aaGGGACGGG-W-GTGGAGGGtt |
| dsGs0034 | 9 | ctaGGGACGGG-W-GTGGAGGGtag |
| dsGs0024 | 10 | taaGGGACGGG-W-GTGGAGGGtta |
| dsGs0037 | 11 | aacGGGACGGG-W-GTGGAGGGgtt |
| dsGs0036 | 12 | ttaGGGACGGG-W-GTGGAGGGtaa |
| dsGs0058 | 13 | ccgGGGACGGG-W-GTGGAGGagg |
| dsGs0008 | 14 | taGGGACGGG-W-GTGGAGGGta |
| dsGs0021 | 15 | aaaGGGACGGG-W-GTGGAGGGttt |
| dsGs0056 | 16 | taGGGGACGGG-W-GTGGAGGGcta |
| dsGs0033 | 17 | ataGGGACGGG-W-GTGGAGGGtat |
| dsGs0003 | 13 | gGGGACGGG-W-GTGGAGGGc |
| dsGs0015 | 19 | ggGGGACGGG-W-GTGGAGGGcc |
| dsGs0023 | 20 | gaaGGGACGGG-W-GTGGAGGGttc |
| dsGs0054 | 21 | cagGGGACGGG-W-GTGGAGGGctg |
| dsGs0019 | 22 | gtGGGACGGG-W-GTGGAGGGac |
| dsGs0000 | 23 | GGGACGGG-W-GTGGAGGG |
| dsGs0001 | 24 | aGGGACGGG-W-GTGGAGGGt |

The combinations 1 to 24 summarized in Table 1 are sequences in each of which $(N)_{n1}$ and $(N)_{m1}$ serving as stem regions are changed into 0 to 3-mer sequences, $(N)_{n2}$ and $(N)_{m2}$ serving as inner loop regions are respectively set as a 2-mer sequence of AC and a 1-mer sequence of A, $(N)_{n3}$ and $(N)_{m3}$ serving as G regions are respectively set as a 3-mer sequence of GGG and a 4-mer sequence of GTGG, and there is no limitation on W.

TABLE 2

| Sequence Name | combination SEQ ID NO: | Sequence 5'- d1         d2 -3' |
|---|---|---|
| dsGm0853 | 25 | aGGGTGGAG-W-GGGTAGGGt |
| dsGm0847 | 26 | aGGGTGAGG-W-GGGAGGGt |
| dsGm0915 | 27 | aGGGTGAGG-W-GGGCCGGGt |
| dsGm0846 | 28 | aGGGTGAGG-W-GGGTAGGGt |
| dsGm1056 | 29 | aGGGTGAGG-W-GGGTTGGGt |
| dsGm1053 | 30 | aGGGTTGAGG-W-GGGTGGGt |
| dsGm0984 | 31 | aGGGTGAGG-W-GGGAGGGGt |
| dsGm0850 | 32 | aGGGTTGGAG-W-GGGAGGGt |
| dsGm0563 | 33 | aGGGGTGAGG-W-GGGAGGGt |
| dsGm0843 | 34 | aGGGTTGAGG-W-GGGAGGGt |
| dsGm0914 | 35 | aGGGTGAGG-W-GGGACGGGt |
| dsGm1063 | 35 | aGGGTGGAG-W-GGGTTGGGt |
| dsGm1060 | 37 | aGGGTTGGAG-W-GGGTGGGt |
| dsGm1054 | 38 | aGGGTGAGG-W-GGGATGGGt |
| dsGm0845 | 39 | aGGGTGAGG-W-GGGCAGGGt |
| dsGm0874 | 40 | aGGGTGCGG-W-GGGTAGGGt |
| dsGm0922 | 41 | aGGGTGGAG-W-GGGCCGGGt |
| dsGm1055 | 42 | aGGGTGAGG-W-GGGCTGGGt |
| dsGm0844 | 43 | aGGGTGAGG-W-GGGAAGGGt |
| dsGm0913 | 44 | aGGGTTGAGG-W-GGGCGGGt |
| dsGm0990 | 45 | aGGGTTGGAG-W-GGGGGGGt |
| dsGm1112 | 46 | aGGGTGTGG-W-GGGTTGGGt |
| dsGm0773 | 47 | aGGGGTGAGG-W-GGGTGGGt |
| dsGm1052 | 48 | aGGGTCGAGG-W-GGGTGGGt |
| dsGs0006 | 49 | caGGGTGAGG-W-GGGAGGGtg |
| _Gm0847 | | |

The combinations 25 to 48 summarized in Table 2 are sequences in each of which $(N)_{n1}$ and $(N)_{m1}$ serving as stem regions are respectively changed into 1-mer sequence of A and 1-mer sequence of T, $(N)_{n2}$ and $(N)_{m2}$ serving as inner loop regions each are changed into a 1 or 2-mer sequence, $(N)_{n3}$ and $(N)_{m3}$ serving as G regions are respectively set as a 4-mer sequence of GAGG, GGAG, GCGG, or GTGG and a 3-mer sequence of GGG, and there is no limitation on W. The combination 49 summarized in Table 2 is a sequence in which $(N)_{n1}$ and $(N)_{m1}$ serving as stem regions are respectively set as a 2-mer sequence of CA and a 2-mer sequence of TG, $(N)_{n2}$ and $(N)_{m2}$ serving as inner loop regions are respectively set as a 1-mer sequence of T and a 1-mer sequence of A, $(N)_{n3}$ and $(N)_{m3}$ serving as G regions are respectively set as a 4-mer sequence of GAGG and a 3-mer sequence of GGG, and there is no limitation on W.

Figure 6:
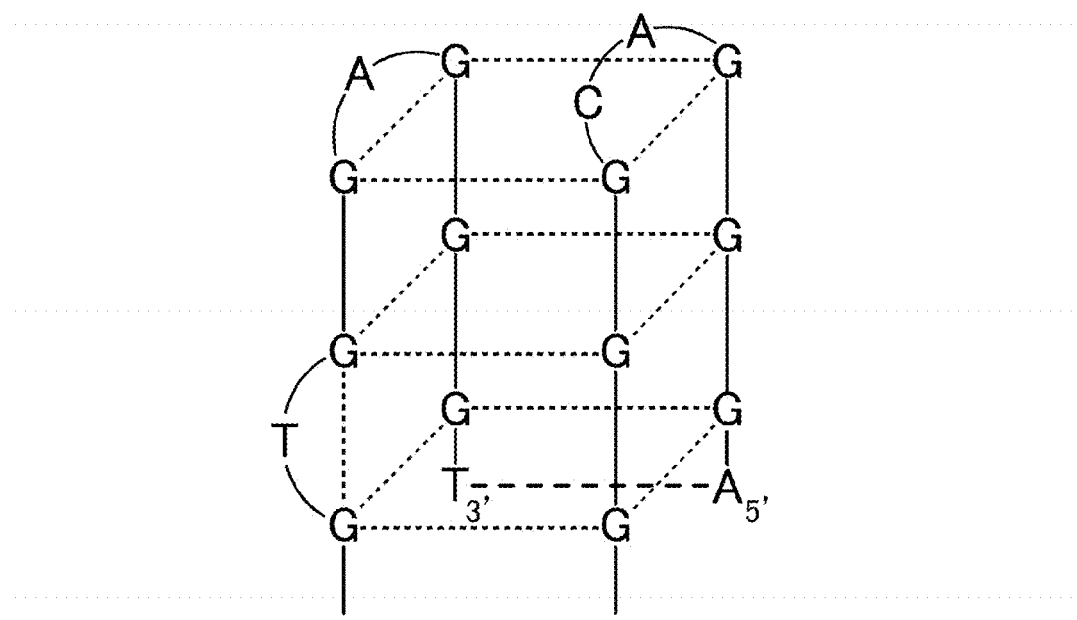
FIG. 6 is a schematic view showing an example of a G-quartet in the sensor of the present invention.

With reference to the G-quartet formed of the first region (D1) and the second region (D2) in the nucleic acid molecule (IV) in the presence of a target, the combination 24 (SEQ ID NO: 24) is shown in FIG. 6 as an example. FIG. 6 is a schematic view showing the G-quartet formed of the first region (D1) and the second region (D2) in the single-stranded nucleic acid molecule of the combination 24 (SEQ ID NO: 24). As shown in FIG. 6, a guanine quadruplex in which three planes of G-quartet are stacked on top of each other between G in the first region (D1) and G in the second region (D2) is formed. However, the present invention is not limited to this example.

The length of the nucleic acid molecule (IV) is not particularly limited. The lower limit of the length is, for example, 25-mer, 30-mer, or 35-mer. The upper limit of the length is, for example, 200-mer, 100-mer, or 80-mer. The range of the length is, for example, from 25- to 200-mer, from 30- to 100-mer, or from 35- to 80-mer.

The nucleic acid molecule (IV) may further include the additional linker region(s) at one end or both ends. The length of the additional linker region is not particularly limited and is, for example, as described above.

One end of the nucleic acid molecule (IV) may be linked to a base material via the additional linker region, for example.

(5) Nucleic Acid Molecule (V)

The nucleic acid molecule (V) is a double-stranded nucleic acid molecule including a first strand (ss1) and a second strand (ss2). The first strand (ss1) includes the G-quartet-forming region (D) and the binding region (A) in this order and the second strand (ss2) includes a stem-forming region ($S_D$) and a stem-forming region ($S_A$) in this order. The stem-forming region ($S_D$) and the G-quartet-forming region (D) include sequences complementary to each other and the stem-forming region ($S_A$) and the binding region (A) include sequences complementary to each other.

In the nucleic acid molecule (V), the G-quartet-forming region (D) is, for example, a single-stranded nucleic acid molecule.

The formation of a G-quartet in the G-quartet-forming region (D) in the nucleic acid molecule (V) is controlled to be switched-ON or switched-OFF depending on the presence or absence of a target on the basis of the following mechanism, for example. The present invention, however, is not limited to this mechanism. In the nucleic acid molecule (V) in the absence of a target, formation of a G-quartet in the G-quartet-forming region (D) is inhibited by annealing of the G-quartet-forming region (D) of the first strand (ss1) and the stem-forming region ($S_D$) of the second strand (ss2) within the molecule, resulting in inhibition of formation of a complex of the G-quartet-forming region (D) and porphyrin (switched-OFF). Furthermore, the structure of the binding region (A) is immobilized by annealing of the binding region (A) of the first strand (ss1) and the stem-forming region ($S_A$) of the second strand (ss2) within the molecule. The molecule structure in this state is also called an inactive form. On the other hand, in the nucleic acid molecule (V) in the presence of a target, the annealing of the binding region (A) and the stem-forming region ($S_A$) is released due to the contact between the target and the binding region (A), and the conformation of the binding region (A) changes into a more stable conformation. In accordance with this, the annealing of the G-quartet-forming region (D) and the stem-forming region ($S_D$) is released and a G-quartet is formed within the region of the G-quartet-forming region (D), resulting in formation of a complex of the G-quartet-forming region (D) and porphyrin, thereby generating fluorescence (switched-ON). The molecule structure in this state is also called an active form. Thus, according to the nucleic acid molecule (V), since fluorescence owing to formation of the complex is not generated in the absence of a target and fluorescence owing to formation of the complex is generated only in the presence of a target, it is possible to perform target analysis such as qualitative analysis or quantitative analysis.

It is preferred that the whole or a part of the stem-forming region ($S_D$) has a sequence complementary to a part of the G-quartet-forming region (D), for example. It is also preferred that the whole or a part of the stem-forming region ($S_A$) has a sequence complementary to a part of the binding region (A), for example.

In the nucleic acid molecule (V), the order of the regions can be any order as long as it allows the annealing of the G-quartet-forming region (D) and the stem-forming region ($S_D$) and the annealing of the binding region (A) and the stem-forming region ($S_A$) within the molecule. Specific examples of the order of the regions are as follows.

(1) ss1 5'-A-D-3'
ss2 3'-$S_A$-$S_D$-5'
(2) ss1 5'-D-A-3'
ss2 3'-$S_D$-$S_A$-5'

In the form (1), it is preferred that the stem-forming region ($S_A$) is complementary to the 3' side region of the binding nucleic acid molecule (A) and the stem-forming region ($S_D$) is complementary to the 5' side region of the G-quartet-forming molecule (D). In the form (2), it is preferred that the stem-forming region ($S_D$) is complementary to the 3' side region of the G-quartet-forming molecule (D) and the stem-forming region ($S_A$) is complementary to the 5' side region of the binding nucleic acid molecule (A).

In the nucleic acid molecule (V), for example, the regions may be linked directly or indirectly. The direct link means that the 3' end of one region and the 5' end of the other region are bound directly, for example. The indirect link means that the 3' end of one region and the 5' end of the other region are bound via an intervening linker region, for example. The intervening linker region may be, for example, a nucleic acid sequence or a non-nucleic acid sequence, and the former is preferable.

It is preferred that the nucleic acid molecule (V) includes the intervening linker region between the binding nucleic acid molecule (A) and the G-quartet-forming molecule (D) in the first strand (ss1) and includes the intervening linker region between the stem-forming region ($S_D$) and the stem-forming region ($S_A$) in the second strand (ss2), for example. It is preferred that the intervening linker region ($L_1$) in the first strand (ss1) and the intervening linker region ($L_2$) in the second strand (ss2) have sequences not complementary to each other.

Specific examples of the order of regions in the case where the forms (1) and (2) each includes the intervening linker regions in the first strand (ss1) and the second strand (ss2) are as follows. In each of the following examples, an intervening linker region that links the binding nucleic acid molecule (A) and the G-quartet-forming molecule (D) is indicated by ($L_1$) and an intervening linker region that links the stem-forming region ($S_D$) and the stem-forming region ($S_A$) is indicated by ($L_2$). The nucleic acid molecule (V) may include both of ($L_1$) and ($L_2$) or either one of ($L_1$) and ($L_2$) as the intervening linker region, for example.

(1') ss1 5'-A-$L_1$-D-3'
ss2 3'-$S_A$-$L_2$-$S_D$-5'
(2') ss1 5'-D-$L_1$-A-3'
ss2 3'-$S_D$-$L_2$-$S_A$-5'

In the forms (1') and (2'), for example, switching-ON and switching-OFF of formation of a G-quartet is performed as follows, for example. In the absence of a target, for example, the binding nucleic acid molecule (A) and the stem-forming region ($S_A$) form a stem and the G-quartet-forming molecule (D) and the stem-forming region ($S_D$) form a stem, and the intervening linker region ($L_1$) and the intervening linker region ($L_2$) form an internal loop between these two stems, thereby inhibiting formation of a G-quartet in the G-quartet-forming molecule (D). In the presence of a target, the formation of each stem is released due to the contact between the target and the binding nucleic acid molecule (A), thereby forming a G-quartet in the G-quartet-forming molecule (D).

Figure 7A:
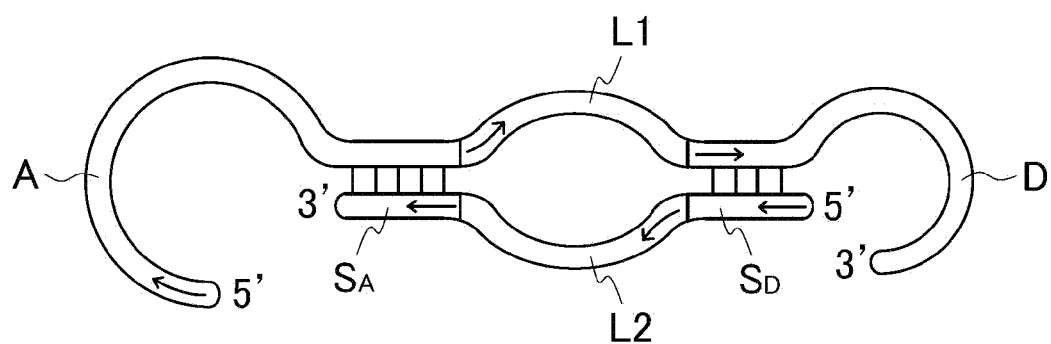
FIGS. 7A and 7B are schematic views showing still another example of a nucleic acid molecule in the sensor of the present invention.
Figure 7B:
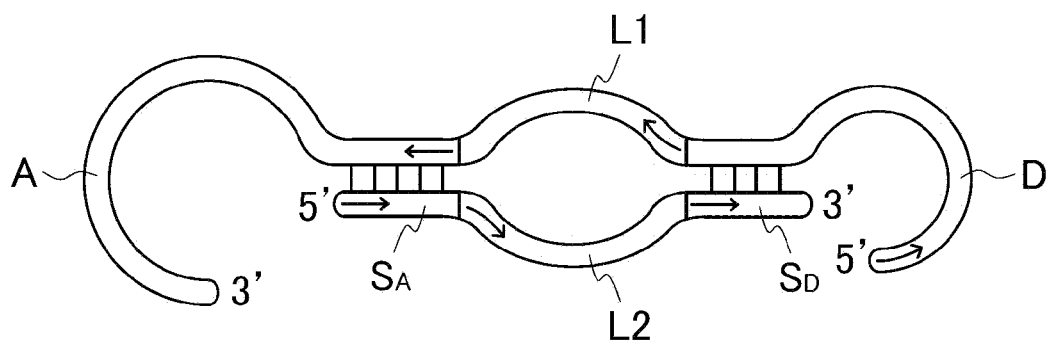

With reference to the forms (1') and (2'), examples of the state of the nucleic acid molecule (V) in the absence of a target are shown in schematic views of FIGS. 7A and 7B. The order of the regions in the nucleic acid molecule (V) shown in FIG. 7A and the order of the regions in the nucleic acid molecule (V) shown in FIG. 7B are in reverse. FIG. 7A shows the form (1') and FIG. 7B shows the form (2').

In FIGS. 7A and 7B, A indicates the binding nucleic acid molecule (A), L1 indicates the intervening linker region (L1), $S_D$ indicates the stem-forming sequence ($S_D$), D indicates the G-quartet-forming molecule (D), L2 indicates the intervening linker region (L2), and $S_A$ indicates the stem-forming sequence ($S_A$). As shown in FIGS. 7A and 7B, in the absence of a target, stems are formed at two positions by annealing of the first strand (ss1) and the second strand (ss2) of the nucleic acid molecule (IV) and an internal loop is formed between the stems. Furthermore, in the presence of a target, the formation of the two stems are released due to the contact between the target and the binding nucleic acid molecule (A), resulting in formation of a G-quartet in the G-quartet-forming molecule (D) and formation of a complex of the G-quartet-forming molecule (D) and porphyrin, thereby generating fluorescence.

In the nucleic acid molecule (V), the lengths of the stem-forming sequence ($S_A$) and the stem-forming sequence ($S_D$) are not particularly limited. The length of the stem-forming sequence ($S_A$) is, for example, from 1- to 60-mer, from 1- to 10-mer, or from 1- to 7-mer. The length of the stem-forming sequence ($S_D$) is, for example, from 1- to 30-mer, from 0- to 10-mer, from 1- to 10-mer, from 0- to 7-mer, or from 1- to 7-mer. The length of the stem-forming sequence ($S_A$) may be, for example, the same as that of the stem-forming sequence ($S_D$), or the former may be longer than the latter or vice versa.

The lengths of the intervening linker regions ($L_1$) and ($L_2$) are not particularly limited. The length of each of the intervening linker regions ($L_1$) and ($L_2$) is, for example, from 0- to 30-mer, from 1- to 30-mer, from 1- to 15-mer, or from 1- to 6-mer. The length of the intervening linker region ($L_1$) may be the same as or different from that of the intervening linker region ($L_2$), for example. In the latter case, the difference between the length of the intervening linker region ($L_1$) and the length of the intervening linker region ($L_2$) is not particularly limited, and is, for example, from 1- to 10-mer, 1- or 2-mer, or 1-mer.

In the nucleic acid molecule (V), the lengths of the first strand (ss1) and the second strand (ss2) are not particularly limited. The length of the first strand (ss1) is, for example, from 40- to 200-mer, from 42- to 100-mer, or from 45- to 60-mer. The length of the second strand (ss2) is, for example, from 4- to 120-mer, 5- to 25-mer, or 10- to 15-mer.

The single-stranded nucleic acid molecule (V) may further include the additional linker regions at one end or both ends of the first strand (ss1) and the second strand (ss2). The length of the additional linker region is not particularly limited and is, for example, as described above.

With reference to the nucleic acid molecule (V), one end of the first strand (ss1) or the second strand (ss2) may be linked to a base material via the additional linker region, for example.

(6) Nucleic acid molecule (VI)

In the present invention, the nucleic acid molecule may be, for example, the following nucleic acid molecule (VI). The nucleic acid molecule (VI) is a single-stranded nucleic acid molecule including the G-quartet-forming region (D) and the binding region (A) in this order. The G-quartet-forming region (D) and the binding region (A) include sequences complementary to each other.

In the nucleic acid molecule (VI), the G-quartet-forming region (D) is, for example, a single-stranded nucleic acid molecule.

The formation of a G-quartet in the G-quartet-forming region (D) in the nucleic acid molecule (VI) is controlled to be switched-ON or switched-OFF depending on the presence or absence of a target on the basis of the following mechanism, for example. The present invention, however, is not limited to this mechanism. In the nucleic acid molecule (I) in the absence of a target, formation of a G-quartet in the G-quartet-forming region (D) is inhibited by annealing of the G-quartet-forming region (D) and the binding region (A) within the molecule, resulting in inhibition of formation of a complex of the G-quartet-forming region (D) and porphyrin (switched-OFF). The molecule structure in this state is also called an inactive form. On the other hand, in the nucleic acid molecule (I) in the presence of a target, the conformation of the binding region (A) changes into a more stable conformation due to the contact between the target and the binding region (A). In accordance with this, the annealing of the G-quartet-forming region (D) and the binding region (A) within the region is released and a G-quartet is formed within the region of the G-quartet-forming region (D), resulting in formation of a complex of the G-quartet-forming region (D) and porphyrin, thereby generating fluorescence (switched-ON). The molecule structure in this state is also called an active form. Thus, according to the sensor of the present invention, since fluorescence owing to formation of the complex is not generated in the absence of a target and fluorescence owing to formation of the complex is generated only in the presence of a target, it is possible to perform target analysis such as qualitative analysis or quantitative analysis.

In the nucleic acid molecule (VI), it is preferred that a sequence in the G-quartet-forming region (D) from the 5' side is complementary to a sequence in the binding region (A) from the 3' side. The complementary sequence in the G-quartet-forming region (D) and the complementary sequence in the binding region (A) each can be referred to as a stem-forming region (S). The former complementary sequence in the G-quartet-forming region (D) can be referred to as a stem-forming region ($S_A$) that forms a stem with the binding region (A) and the latter complementary sequence in the binding region (A) can be referred to as a stem-forming region ($S_D$) that forms a stem with the G-quartet-forming region (D). It is preferred that a part of the G-quartet-forming region (D) is, for example, the complementary sequence, i.e., the stem-forming region ($S_A$), and a part of the binding region (A) is, for example, the complementary sequence, i.e., the stem-forming region ($S_D$). The position of the complementary sequence in the G-quartet-forming region (D) and the position of the complementary sequence in the binding region (A) are not particularly limited.

In the nucleic acid molecule (VI), the lengths of the complementary sequences between the G-quartet-forming molecule (D) and the binding nucleic acid molecule (A) are not particularly limited. The length of each of the complementary sequences is, for example, from 1- to 30-mer, from 1- to 10-mer, or from 1- to 7-mer.

In the nucleic acid molecule (VI), for example, the G-quartet-forming region (D) and the binding region (A) may be linked directly or indirectly. The direct link means that the 3' end of one region and the 5' end of the other region are bound directly, for example. The indirect link means that the 3' end of one region and the 5' end of the other region are bound via a linker region, for example.

Hereinafter, the linker region that links the regions is also referred to as an intervening linker region. The intervening linker region may be, for example, a nucleic acid sequence or a non-nucleic acid sequence, and the former is preferable. The length of the intervening linker region is not particularly limited, and is, for example, from 0- to 20-mer, from 1- to 10-mer, or from 1- to 6-mer.

One end of the nucleic acid molecule (VI) may be linked to a base material via the additional linker region, for example.

The length of the nucleic acid molecule (VI) is not particularly limited. The length of the nucleic acid molecule (VI) is, for example, from 40- to 120-mer, from 45- to 100-mer, or from 50- to 80-mer.

The sensor of the present invention may be a molecule including the aforementioned nucleic acid molecule or a molecule composed of the aforementioned nucleic acid.

The sensor of the present invention is a molecule including a nucleotide residue, and may be, for example, a molecule consisting of a nucleotide residue or a molecule including a nucleotide residue. Examples of the nucleotide include ribonucleotide, deoxyribonucleotide, and derivatives thereof. Specifically, the sensor may be, for example, DNA including deoxyribonucleotide and/or a derivative thereof, RNA including ribonucleotide and/or a derivative thereof, or chimera (DNA/RNA) including the former and the latter. It is preferred that the sensor is DNA.

The nucleotide may include, for example, either a natural base (non-artificial base) or a non-natural base (artificial base). Examples of the natural base include A, C, G, T, and U and modified bases thereof. Examples of the modification include methylation, fluorination, amination, and thiation. Examples of the non-natural base include 2'-fluoropyrimidine and 2'-O-methylpyrimidine, and specific examples thereof include 2'-fluorouracil, 2'-aminouracil, 2'-O-methyluracil, and 2-thiouracil. The nucleotide may be, for example, modified nucleotide, and examples of the modified nucleotide include 2'-methylated-uracil nucleotide residue, 2'-methylated-cytosine nucleotide residue, 2'-fluorinated-uracil nucleotide residue, 2'-fluorinated-cytosine nucleotide residue, 2'-aminated-uracil-nucleotide residue, 2'-aminated-cytosine nucleotide residue, 2'-thiated-uracil nucleotide residue, and 2'-thiated-cytosine nucleotide residue. The candidate molecule may include non-nucleotide such as peptide nucleic acid (PNA) or locked nucleic acid (LNA), for example.

The porphyrin is not particularly limited, and examples thereof include unsubstituted porphyrin and a derivative thereof. Examples of the derivative include substituted porphyrin and a metal porphyrin obtained by forming a complex of porphyrin and a metal element. Examples of the substituted porphyrin include N-Methylmesoporphyrin (NMM), TMPyP (5, 10, 15, 20-tetrakis(N-methyl pyridinium-4-yl)-21H, 23H-porphyrin, tetrakis(p-toluene sulfonate)). The metal porphyrin can be, for example, iron porphyrin, zinc porphyrin, and the like. Specific examples of the metal porphyrin include Zn-DIGP (tetrakis-(diisopropyl-guanidino) zinc phthalocyanine), and ZnPP9 (Zinc(H) protoporphyrin D). The porphyrin is preferably NMM, for example.

The sensor of the present invention may be in the state where the nucleic acid molecule is free or in the state where the nucleic acid molecule is immobilized, for example. In the latter case, for example, the nucleic acid molecule is immobilized on the base material, which can be used as a device. Examples of the base material include substrates such as a plate, a sheet, a film, and a swab; containers such as a well plate and a tube; beads; particles; and filters. Either the 5' end or the 3' end of the nucleic acid molecule may be immobilized, for example.

There is no particular limitation on the immobilization method, and a linkage by a chemical bond can be employed. Specifically, the immobilization method can be, for example, a method of binding streptavidin or avidin to one of the base material and the nucleic acid molecule and binding biotin to the other and utilizing the bond between the former and the latter.

As the immobilization method, a known nucleic acid immobilization method can be employed besides the above-mentioned method, for example. The known nucleic acid immobilization method can be, for example, a method utilizing photolithography. As a specific example, the method can be referred to the specification of U.S. Pat. No. 5,424,186. The immobilization method can be, for example, a method in which the nucleic acid molecule is synthesized on the base material. This method can be, for example, a so-called spot method. As a specific example, the method can be referred to the specification of U.S. Pat. No. 5,807,522 or JP H10(1998)-503841 A.

The nucleic acid molecule may be directly or indirectly immobilized on the base material, for example. In the former case, for example, it is preferred that the end of the nucleic acid molecule is immobilized on the base material. In the latter case, for example, the nucleic acid molecule may be immobilized on the base material via a linker for immobilization. The linker may be, for example, a nucleic acid sequence or a non-nucleic acid sequence, and can be the aforementioned additional linker region or the like. In the case where the nucleic acid molecule is immobilized on the base material, a site on which the nucleic acid molecule is disposed is also referred to as a detection part in the sensor.

The sensor of the present invention may include a plurality of detection parts, for example. In this case, in the sensor, it is preferred that the surface of the base material is fractionated into matrix, and each fraction region is provided with each of the above-mentioned detection parts, for example. In the sensor of the present invention, the number of nucleic acid sensors arranged in one detection part is not particularly limited.

The sensor of the present invention may further include a reagent part that contains a reagent, for example. The reagent includes porphyrin, for example. The reagent part can be disposed on the base material, for example. A site of the base material on which the reagent part is disposed may be the same as or different from the site on which the nucleic acid molecule is disposed, for example. In the latter case, the site on which the reagent part is disposed can be anywhere as long as the reagent in the reagent part comes into contact with the sensor by addition of a sample, for example.

The usage of the sensor of the present invention is not particularly limited, and can be used for the target analysis method of the present invention as follows.

2. Target Analysis Method

As described above, the target analysis method according to the present invention is characterized in that it includes steps of: bringing a sample into contact with the fluorescence sensor for target analysis according to the present invention; and detecting fluorescence generated by a complex of the G-quartet-forming region (D) and porphyrin in the sensor in the presence of porphyrin to detect a target in the sample.

The sample is not particularly limited. The sample may be, for example, either one of a sample containing a target and a sample in which the presence of a target is unknown. The sample is preferably a liquid sample, for example. In the case where a specimen is, for example, liquid, the specimen may be used as a sample without processing or a dilute solution obtained by mixing a specimen with a solvent may be used as a sample. In the case where a specimen is, for example, solid, powder, or the like, a mixture obtained by mixing a specimen with a solvent, a suspension obtained by suspending a specimen in a solvent, or the like may be used as a sample. The solvent is not particularly limited, and examples thereof include water and buffer solutions. Examples of the specimen include those collected from a living body, soil, seawater, river water, wastewater, food and beverage, purified water, and air.

Specific examples of the sample include raw milk, processed milk, and milk powder. In the case where non-protein or non-lipid in the sample is a target, for example, the sensor of the present invention allows analysis of the target in the sample without performing pretreatment of removing protein or lipid from the sample.

When the nucleic acid molecule in a free state is used as the sensor of the present invention, it is preferred that the sensor and the sample are caused to be in contact with each other in a container, for example. When the nucleic acid molecule immobilized on the base material is used as the sensor of the present invention, the sample can be caused to be in contact with the sensor on the base material, for example.

The detection step is a step of detecting fluorescence from the sensor in the presence of porphyrin, for example. The fluorescence may be visually detected or the fluorescence intensity may be detected, for example.

In the detection of fluorescence intensity, the excitation wavelength is, for example, from 350 to 550 nm, from 350 to 450 nm, or 399 nm, and the emission wavelength is, for example, from 550 to 700 nm, from 550 to 650 nm, or 605 nm.

In the analysis method of the present invention, for example, the porphyrin may be caused to coexist with the sensor in the contact step or may be caused to coexist with the sensor in the subsequent detection step. In the former case, for example, porphyrin may be supplied to the sensor before bringing the sample into contact with the sensor or at the same time as the contact between the sample and the sensor. In this case, for example, porphyrin may be preliminarily disposed on the reagent part of the sensor as described above. On the other hand, in the latter case, porphyrin may be supplied to the sensor after bringing the sample into contact with the sensor.

The form of porphyrin when it is supplied to the sensor is not particularly limited. It is preferred that the porphyrin is supplied to the sensor in the form of a reagent liquid obtained by mixing porphyrin with a liquid, for example. The liquid to be mixed with the porphyrin is preferably a buffer solution such as Tris-HCl or the like, for example. The concentration of the porphyrin in the reagent liquid is not particularly limited and is, for example, from 50 to 500 mmol/L or from 100 to 300 mmol/L. The pH of the reagent liquid is, for example, from 6 to 9, or from 6.8 to 9.

The time for the contact step is not particularly limited and is, for example, from 1 to 30 minutes. The treatment time from the contact between the sensor, the sample, and the porphyrin in the contact step to the detection of fluorescence in the detection step is, for example, from 1 to 30 minutes. The temperature condition in the contact step and the detection step is not particularly limited and is, for example, from 15° C. to 37° C.

The analysis method of the present invention may further include a washing step between the contact step and the detection step. The washing step is a step of washing the sensor with a washing liquid after bringing the sensor into contact with the sample, for example. The washing step allows impurities contained in the sample to be removed and allows an analysis with superior accuracy, for example. The washing liquid is not particularly limited and examples thereof include aqueous solvents such as water, buffer solutions, and the like. For example, the sensor is preferably the one in which the nucleic acid molecule is immobilized on the base material because such a structure allows the washing step to be performed easily.

A G-quartet is formed in a G-quartet-forming region (D), a complex of the G-quartet-forming region (D) and porphyrin is formed, and fluorescence generated by the complex is detected in the present invention as described above. Thus, it can be said that light emission of the sensor itself is detected in the present invention. Therefore, unlike the sensor in the art, the present invention does not require a substrate for catalytic reaction for measuring the catalytic activity of a catalyst molecule such as DNAzyme or the like, for example. Examples of such a substrate include a substrate that develops a color, fluorescence, or the like and a substrate that quenches its color, fluorescence, or the like.

3. Analysis Kit

As described above, the analysis kit according to the present invention is characterized in that it includes: a sensor; and a reagent. The sensor is the fluorescence sensor for target analysis according to the present invention, and the reagent includes porphyrin. The analysis kit according to the present invention is characterized in that it includes the sensor and porphyrin, and there is no limitation on the configuration other than this.

The analysis kit of the present invention may include, besides the sensor and porphyrin, for example, components such as the buffer solution, the base material, and the like.

In the analysis kit of the present invention, for example, the sensor and the reagent may be contained separately, for example. In the case where the analysis kit of the present invention further includes other components as described above, these components may be contained separately from the sensor, for example. In the sensor, the nucleic acid molecule may be immobilized on the base material or the nucleic acid molecule may not be immobilized, for example. The analysis kit may further include, for example, an instruction manual.

Hereinafter, the present invention will be described in detail with reference to examples. It is to be noted, however, that the present invention is not limited thereto.

EXAMPLES

Example 1

A fluorescence sensor for melamine analysis was produced using melamine aptamer as a binding nucleic acid molecule (A) and single-stranded DNAzyme as a G-quartet-forming molecule (D).

A fluorescence sensor for melamine analysis corresponding to the nucleic acid molecule (I) was produced. The sequence of the fluorescence sensor is shown below. In the sequence below, the underlined part at the 5' side is DNAzyme and the underlined part at the 3' side is melamine aptamer. The boxed sequences are complementary to each other. The fluorescence sensor changes into a blocking form when the complementary sequences form a stem in the absence of melamine.

TABLE 3

(SEQ ID NO 50)
fluorescence sensor
5'-TGGGTGGGAGGGTCGGGCCCTCCCGGTTTTTTTTTTTT
TTTTTTTTTTTTTTTTTGCGG-3'

Example 2

Detection of melamine in milk was performed using the fluorescence sensor for melamine analysis of Example 1.
Buffer solution A: 50 mmol/L Tris-HCl (pH 7.4),
  20 mmol/L KCl, and
  0.05% (w/v) TritonX-100
Buffer solution B: 50 mmol/L Tris-HCl (pH 7.4),
  20 mmol/L KCl,
  0.05% (w/v) TritonX-100, and
  50 mmol/L EDTA The fluorescence sensor was suspended in the buffer solution B to prepare a sensor reagent and NMM was suspended in the buffer solution B to prepare a NMM reagent. With commercially available milk (raw milk: 100%, product name: Meiji Oishii Gyunyu, Meiji Holdings Co., Ltd.) being a 100% sample, dilute solutions each obtained by diluting the commercially available milk with the buffer solution A of Example 1 were used as dilute samples.

First, the sensor reagent was added to a 1.5 mL-tube and treated at 95° C. for 5 minutes, followed by incubation at room temperature for 15 minutes. Then, the NMM reagent and 25 μL of the sample were added to the tube and incubated at room temperature for 30 minutes. The final concentration of the sensor was 400 nmol/L, the final concentration of the NMM was 200 nmol/L, and the final concentration of the milk was 0 (containing no milk), 10, 20, 30, 40, or 50% in each of 50 μL of the reaction solutions. Reaction solutions were dispensed to wells of a plate (product name: Greiner 384 Flat Bottom Black Polystyrol, Greiner) and the fluorescence intensity was measured. The fluorescence intensity was measured using a microplate reader (product name: TECAN infinite M1000 PRO, TECAN) with the excitation wavelength at 399 nm and the emission wavelength at 550 to 690 nm.

Figure 8A:
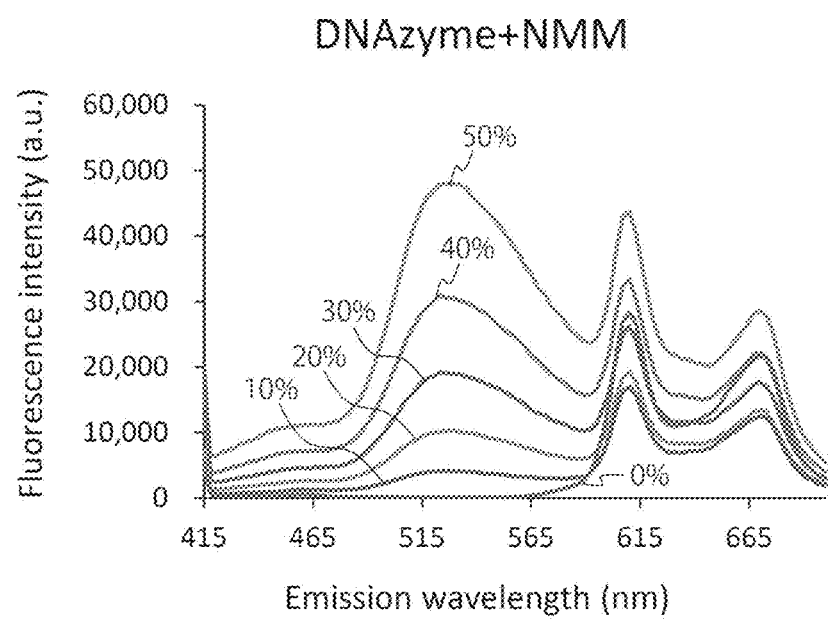
FIGS. 8A and 8B are graphs showing the fluorescence intensity in Example 2 of the present invention.
Figure 8B:
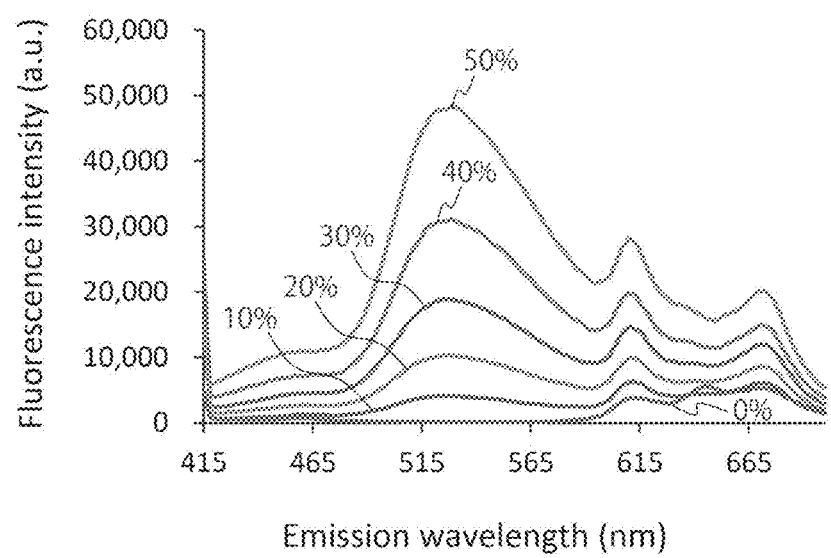

The results are shown in FIGS. 8A and 8B. FIGS. 8A and 8B are graphs showing the fluorescence intensity within the emission wavelength range. FIG. 8A shows the results of reaction solutions each containing a sensor. FIG. 8B shows the results of reaction solutions each containing no sensor. In each graph, the vertical axis indicates the fluorescence intensity, and the horizontal axis indicates the emission wavelength. As shown in FIGS. 8A and 8B, the reaction solutions each containing a sensor shown in FIG. 8A showed higher peak than the reaction solutions each containing no sensor shown in FIG. 8B at the emission wavelength of 605 nm. This result shows that the emission wavelength of 605 nm shows the highest S/N ratio and allows the detection of the fluorescence generated by a complex of the sensor and the NMM in milk.

Example 3

Detection of melamine in milk was performed using the fluorescence sensor for melamine analysis of Example 1.

With commercially available milk (raw milk: 100%, product name: Meiji Oishii Gyunyu, Meiji Holdings Co., Ltd.) being a 100% sample containing no melamine, dilute solutions each obtained by diluting the commercially available milk with the buffer solution A of Example 1 were used as dilute samples containing no melamine. Furthermore, melamine was added to the 100% sample containing no melamine and to the dilute samples each containing no melamine to prepare samples each containing melamine. The fluorescence intensities of reaction solutions each containing a sensor and reaction solutions each containing no sensor were measured in the same manner as in Example 2 except that the samples each containing no melamine and the samples each containing melamine were used as samples and the excitation wavelength was set at 399 nm and the emission wavelength was set at 605 nm as the measurement condition. The final concentration of the milk was 0, 10, 20, 30, 40, or 50% and the final concentration of melamine was 0, 1, 2, 3, or 5 mmol/L in the reaction solutions.

Figure 9A:
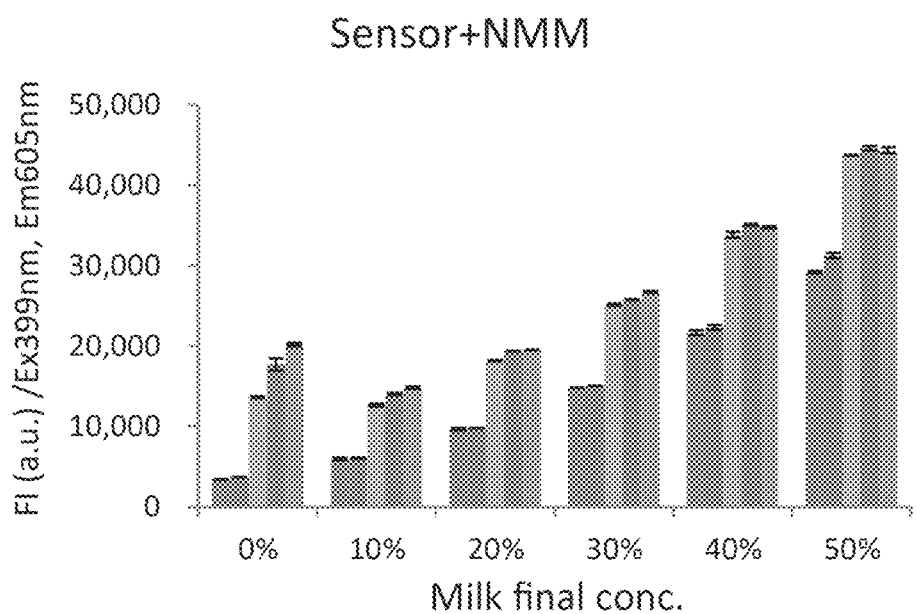
FIGS. 9A and 9B are graphs showing the fluorescence intensity in Example 3 of the present invention.
Figure 9B:
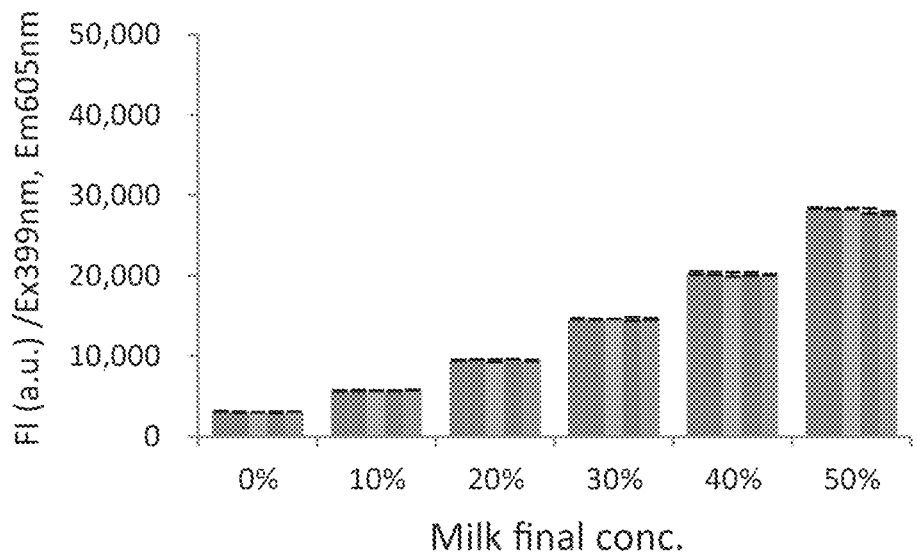

The results are shown in FIGS. 9A and 9B. FIGS. 9A and 9B are graphs showing the fluorescence intensity. FIG. 9A shows the results of reaction solutions each containing a sensor. FIG. 9B shows the results of reaction solutions each containing no sensor. In each graph, the vertical axis indicates the fluorescence intensity. In each graph, the horizontal axis indicates the type of sample. The horizontal axis shows sample sets in which the final concentrations of milk in the reaction solutions are 0, 10, 20, 30, 40, and 50% from the left. In each sample set, the five bars show the samples with the final concentrations of melamine of 0, 1, 2, 3, and 5 mmol/L from the left. As shown in FIG. 9B, with respect to the reaction solutions each containing no sensor, the fluorescence intensities were constant in each sample set in which the milk concentration was standardized regardless of the melamine concentration. In contrast, as shown in FIG. 9A, with respect to the reaction solutions each containing a sensor, the fluorescence intensities were increased as the melamine concentration increases in each sample set. This result shows that the fluorescence sensor of Example allows concentration-dependent detection of melamine in a sample.

The fluorescence intensity of the sample in which the melamine concentration is 0 mmol/L in each sample set shown in FIG. 9A is comparable to the fluorescence intensity of the reaction solution containing no sensor in each sample set shown in FIG. 9B. This shows that the background at the time of using a sensor is low and standardization can be performed by subtracting the fluorescence intensity of the reaction solution containing no sensor from the fluorescence intensity of the reaction solution containing a sensor, for example.

Figure 10:
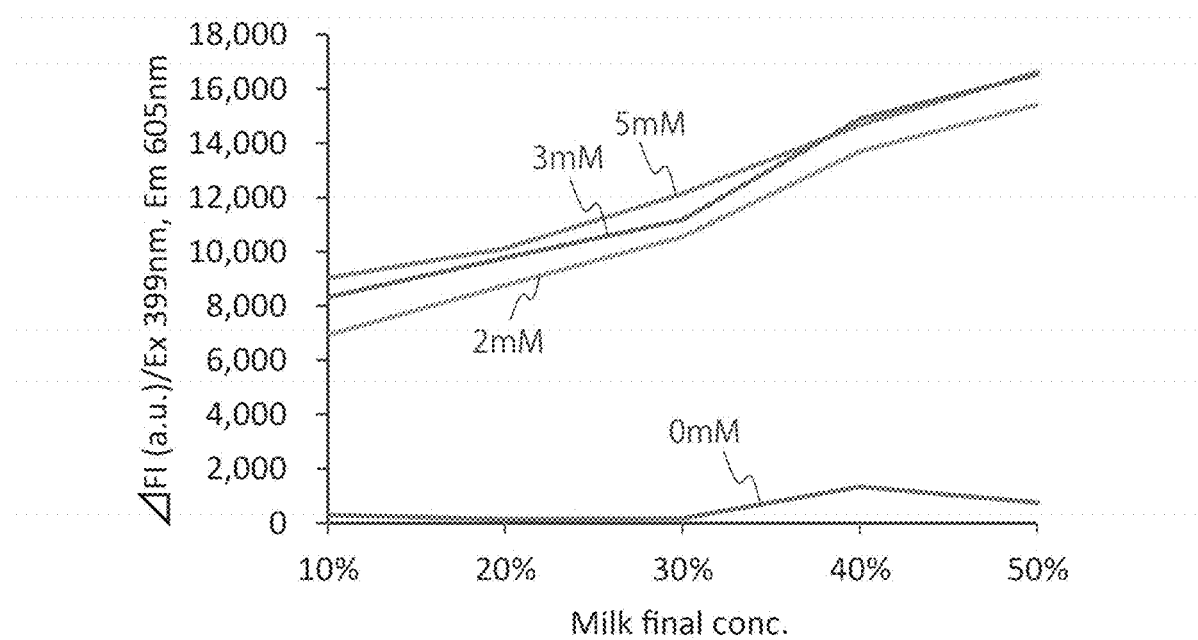
FIG. 10 is a graph showing the difference between the fluorescence intensity of a reaction solution containing a melamine sensor and the fluorescence intensity of a reaction solution containing no melamine sensor in Example 3 of the present invention.

Hence, the results obtained by subtracting the fluorescence intensity of each reaction solution containing no sensor shown in FIG. 9B from the fluorescence intensity of each reaction solution containing a sensor shown in FIG. 9A are shown in FIG. 10.

FIG. 10 is a graph showing the fluorescence intensity which is a value obtained by subtracting the fluorescence intensity of each reaction solution containing no sensor from the fluorescence intensity of each reaction solution containing a sensor. The horizontal axis indicates the final concentration of milk in the reaction solution and each plot indicates the final concentration of melamine in the reaction solution. As shown in FIG. 10, in all the reaction solutions in each of which the final concentration of milk is from 10% to 50%, the fluorescence intensities were remarkably increased owing to the presence of melamine. This result shows that melamine can be detected regardless of the concentration of milk in a sample.

Detection of melamine of 500 ppm (4 mmol/L) or more is generally required in the market. As shown in FIG. 11, sufficient fluorescence intensity was obtained with respect to the reaction solution (final concentration of melamine: 2 mmol/L, final concentration of milk 50%) using 100% milk having 4 mmol/L melamine concentration as a sample. This shows that the accuracy required in the market is sufficiently achieved.

While the present invention has been described above with reference to illustrative embodiments, the present invention is by no means limited thereto. Various changes that may become apparent to those skilled in the art may be made in the configuration and specifics of the present invention without departing from the scope of the present invention.

This application is based upon and claims the benefit of priority from Japanese patent application No. 2013-152476, filed on Jul. 23, 2013, the disclosure of which is incorporated herein its entirety by reference.

INDUSTRIAL APPLICABILITY

According to the fluorescence sensor of the present invention for target analysis, a target can be indirectly analyzed in simple and efficient manner by utilizing generation of fluorescence. Therefore, for example, the present invention is very useful for researches and tests in various fields such as a clinical treatment field, a food field, and an environment field.

[Sequence Listing] TF14016WO_2014.05.19_ST25.txt

The invention claimed is:

1. A fluorescence sensor for target analysis, comprising at least one nucleic acid molecule selected from the group consisting of the following (I), (II), (III), (IV), and (V) each comprising a G-quartet-forming region (D) that forms a G-quartet and a binding region (A) that binds to a target, wherein in an absence of the target, formation of a G-quartet in the G-quartet-forming region (D) is inhibited, and in a presence of the target, the target comes into contact with the binding region (A), the G-quartet is formed in the G-quartet-forming region (D) due to the contact, the G-quartet-forming region (D) and porphyrin form a complex, and the complex generates fluorescence:

(I) a single-stranded nucleic acid molecule comprising the G-quartet-forming region (D), a blocking region (B), and the binding region (A) in this order, wherein the blocking region (B) is complementary to a partial region (Dp) of the G-quartet-forming region (D), and a terminal region (Ab) of the binding region (A) on a blocking region (B) side is complementary to an adjacent region (Df) of the partial region (Dp) of the G-quartet-forming region (D) and is also complementary to a terminal region (Af) of the binding region (A) on an opposite side of the blocking region (B) side;

(II) a single-stranded nucleic acid molecule comprising the G-quartet-forming region (D), a blocking region (B), the binding region (A), and a stabilizing region (S) in this order, wherein the blocking region (B) is complementary to a partial region (Dp) of the G-quartet-forming region (D), and a terminal region (Ba) of the blocking region (B) on a binding region (A) side is complementary to the stabilizing region (S);

(III) a single-stranded nucleic acid molecule comprising the G-quartet-forming region (D), a stem-forming region ($S_D$), the binding region (A), and a stem-forming region (SA), wherein the stem-forming region ($S_D$) includes a sequence complementary to the G-quartet-forming region (D), and the stem-forming region ($S_D$) includes a sequence complementary to the binding region (A) and the nucleic acid molecule (III) includes two intervening linker regions not complementary to each other;

(IV) a single-stranded nucleic acid molecule comprising the G-quartet-forming region (D) and the binding region (A), wherein the G-quartet-forming region (D) comprises a first region (D1) and a second region (D2) that form a G-quartet, and the first region (D1) is located on one end side of the binding region (A) and the second region (D2) is located on the other end side of the binding region (A) and the first region (D1) and the second region (D2) include sequences complementary to each other at the ends on the opposite side of the position of the binding region (A); and (V) a double-stranded nucleic acid molecule comprising a first strand (ss1) and a second strand (ss2), wherein the first strand (ss1) comprises the G-quartet-forming region (D) and the binding region (A) in this order, and the second strand (ss2) comprises a stem-forming region ($S_D$) and a stem-forming region (SA) in this order, the stem-forming region ($S_D$) includes a sequence complementary to the G-quartet-forming region (D), and the stem-forming region ($S_A$) includes a sequence complementary to the binding region (A).

2. The fluorescence sensor according to claim 1, wherein the single-stranded nucleic acid molecule (I) or (II) comprises the G-quartet-forming region (D), the blocking region (B), and the binding region (A) from a 5' side in this order.

3. The fluorescence sensor according to claim 1, wherein the single-stranded nucleic acid molecule (III) comprises the stem-forming region ($S_D$) and the stem-forming region ($S_A$) as the stem-forming region (S), the G-quartet-forming region (D) and the stem-forming region ($S_D$) include sequences complementary to each other, and the binding region (A) and the stem-forming region ($S_A$) include sequences complementary to each other.

4. The fluorescence sensor according to claim 3, wherein in the single-stranded nucleic acid molecule (III), the G-quartet-forming region (D), the stem-forming region ($S_D$), the binding region (A), and the stem-forming region ($S_A$) are linked in the following order (1), (2), (3), or (4):

(1) in order of the binding region (A), the stem-forming region ($S_D$), the G-quartet-forming region (D), and the stem-forming region (SA);

(2) in order of the stem-forming region ($S_A$), the G-quartet-forming region (D), the stem-forming region ($S_D$), and the binding region (A);

(3) in order of the G-quartet-forming region (D), the stem-forming region ($S_A$), the binding region (A), and the stem-forming region ($S_D$); or (4) in order of the stem-forming region ($S_D$), the binding region (A), the stem-forming region (SA), and the G-quartet-forming region (D).

5. The fluorescence sensor according to claim 1, wherein in the single-stranded nucleic acid molecule (IV), the first region (D1) and the second region (D2) include sequences complementary to each other at ends on an opposite side of a position of the binding region (A).

6. The fluorescence sensor according to any one of claims 1 to 5, comprising: a linker sequence between the G-quartet-forming region (D) and the binding region (A).

7. The fluorescence sensor according to any one of claims 1 to 5, further comprising: a base material, wherein the nucleic acid molecule is disposed on the base material.

8. The fluorescence sensor according to claim 7, wherein the nucleic acid molecule is linked to the base material via a linker region.

9. The fluorescence sensor according to any one of claims 1 to 5, wherein a reagent part that contains a reagent is further disposed on the base material, and the reagent includes porphyrin.

10. The fluorescence sensor according to claim 9, wherein the porphyrin is at least one selected from the group consisting of N-Methylmesoporphyrin, Zn-DIGP, ZnPP9, and TMPyP.

11. A kit for target analysis, comprising:
a sensor;
and a reagent, wherein
the sensor is the fluorescence sensor for target analysis according to any one of claims 1 to 10, and
the reagent includes porphyrin.

12. The kit according to claim 11, wherein
the sensor is a sensor in which the nucleic acid molecule is disposed on a base material, and
a reagent part that contains the reagent is further disposed on the base material.

13. The kit according to claim 11 or 12, wherein
the porphyrin is at least one selected from the group consisting of N-Methylmesoporphyrin, Zn-DIGP, ZnPP9, and TMPyP.

14. A method for target analysis, comprising steps of:
bringing a sample into contact with the fluorescence sensor for target analysis according to any one of claims 1 to 10; and
detecting fluorescence generated by a complex of the G-quartet-forming region (D) and porphyrin in the sensor in the presence of porphyrin to detect a target in the sample.

15. The method according to claim 14, wherein
detection of fluorescence in the detection step is measurement of a fluorescence intensity.

16. The method according to claim 14 or 15, wherein
the sample is at least one selected from the group consisting of raw milk, processed milk, and milk powder.

17. The method according to any one of claims 14 to 16, wherein the target is melamine.

\* \* \* \* \*